(12) United States Patent
Stähle et al.

(10) Patent No.: US 8,242,128 B2
(45) Date of Patent: *Aug. 14, 2012

(54) 1,3-BENZOXAZOLYL DERIVATIVES AS KINASE INHIBITORS

(75) Inventors: Wolfgang Stähle, Ingelheim (DE);
Alfred Jonczyk, Darmstadt (DE);
Wilfried Rautenberg, Reinheim (DE)

(73) Assignee: Merck Patent GmbH, Darmstadt (DE)

( * ) Notice: Subject to any disclaimer, the term of this patent is extended or adjusted under 35 U.S.C. 154(b) by 941 days.

This patent is subject to a terminal disclaimer.

(21) Appl. No.: 10/573,176

(22) PCT Filed: Sep. 1, 2004

(86) PCT No.: PCT/EP2004/009743
§ 371 (c)(1),
(2), (4) Date: Mar. 23, 2006

(87) PCT Pub. No.: WO2005/037829
PCT Pub. Date: Apr. 28, 2005

(65) Prior Publication Data
US 2006/0281762 A1    Dec. 14, 2006

(30) Foreign Application Priority Data
Sep. 24, 2003  (DE) .................................. 103 44 223

(51) Int. Cl.
*A61K 31/506* (2006.01)
*A61K 31/423* (2006.01)
*A61K 31/4465* (2006.01)
*C07D 239/42* (2006.01)
*C07D 413/10* (2006.01)
*C07D 263/58* (2006.01)

(52) U.S. Cl. ........ 514/272; 514/338; 514/375; 544/321; 546/271.7; 548/222

(58) Field of Classification Search .................. None
See application file for complete search history.

(56) References Cited

U.S. PATENT DOCUMENTS

| 6,579,857 B1 * | 6/2003 | Lind et al. ................. 514/46 |
| 7,041,691 B1 * | 5/2006 | McGee et al. ............... 514/367 |
| 7,470,702 B2 * | 12/2008 | Staehle et al. .............. 514/277 |
| 2002/0156081 A1 | 10/2002 | Hirst et al. |
| 2003/0225131 A1 * | 12/2003 | Burgey et al. ................ 514/318 |
| 2004/0006083 A1 | 1/2004 | Hirst et al. |
| 2004/0082583 A1 | 4/2004 | Cheung et al. |

FOREIGN PATENT DOCUMENTS

| WO | WO02/76960 A1 * | 3/2002 |
| WO | WO 0244156 | 6/2002 |
| WO | WO 02076986 | 10/2002 |
| WO | WO 02080926 | 10/2002 |
| WO | WO 03/082272 | * 10/2003 |

OTHER PUBLICATIONS

Morissette et al. "High-throughput crystallization: polymorphs, salts, co-crystals and solvates of pharmaceutical solids." Advanced Drug Delivery Reviews 2004, 56, 275-300.*
Vippagunta, Sudha R. "Crystalline Solids." Advanced Drug Delivery Reviews 48(2001): 3-26.*
Reckhow, David. "Chapter XXII: Miscellaneous Instrumental Methods." University of Massachusetts Amherst, College of Engineering. CEE-572, May 5, 2001.*
"Derivative." Mirriam-Webster OnLine Dictionary. 2009. Merriam-Webster Online. Feb. 11, 2009 <http://www.merriam-webster.com/dictionary/derivative>.*
Patani, et al. Bioisosterism: A Rational Approach in Drug Design, Chem. Rev. 1996, 96, pp. 3147-3176, especially p. 3149.*
Garin et al. J. Het. Chem. 27(2), 1990, pp. 221-226.*
El-Gaby et al, J. Chin. Chem. Soc. (2002), 49, pp. 407-414.*
El-Gaby et al, J. Chin. Chem. Soc. (2004), 51, No. 2, pp. 327-333.*

* cited by examiner

*Primary Examiner* — Rebecca Anderson
*Assistant Examiner* — Alicia L Otton
(74) *Attorney, Agent, or Firm* — Millen, White, Zelano & Branigan, P.C.

(57) ABSTRACT

The invention relates to compounds of formula 1, the production and use thereof as a medicament for the treatment of diseases, particularly tumours and/or diseases caused, mediated or propagated by angiogenesis. The compounds of formula 1 are effective inhibitors of tyrosin kinases, particularly TIE-2 and VEGFR, and Raf-kinases. (I)

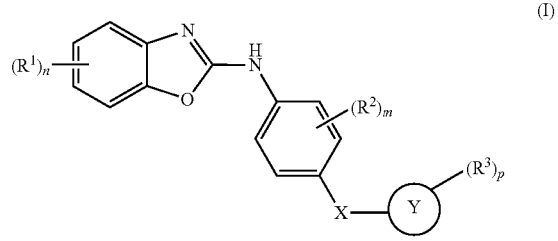

18 Claims, No Drawings

1,3-BENZOXAZOLYL DERIVATIVES AS KINASE INHIBITORS

BACKGROUND OF THE INVENTION

The invention relates to compounds of the formula I

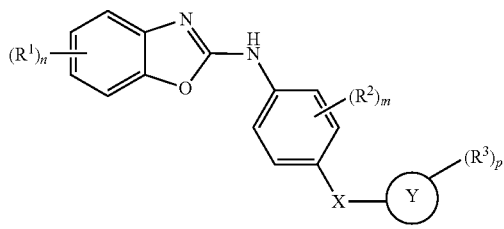

in which
R$^1$, R$^2$, R$^3$ each, independently of one another, denote R, Hal, CN, NO$_2$, NHR, NRR, NHCOR, NHSO$_2$R, OR, CO—R, CO—NHR, CF$_3$, OCF$_3$, SCF$_3$, SO$_3$R, SO$_2$R, SO$_2$NR, SR, COOH or COOR,
R denotes H or unsubstituted or mono-, di-, tri- or tetra-R$^4$-substituted A, Ar, Het, (CH$_2$)$_q$Het or (CH$_2$)$_q$Ar,
A denotes unbranched, branched or cyclic alkyl having 1-14 C atoms, in which one or two CH$_2$ groups may be replaced by O or S atoms and/or by —CH═CH— groups and/or in addition 1-7 H atoms may be replaced by F and/or Cl,
Ar denotes phenyl, naphthyl or biphenyl, each of which is unsubstituted or mono-, di- or trisubstituted by A, Hal, OH, OA, CN, NO$_2$, NH$_2$, NHA, NA$_2$, NHCOA, SCF$_3$, SO$_2$A, COOH, COOA, CONH$_2$, CONHA, CONA$_2$, NHSO$_2$A, SO$_2$NH$_2$, SO$_2$NHA, SO$_2$NA$_2$, CHO or COA,
Het denotes a mono- or bicyclic saturated, unsaturated or aromatic heterocycle having 1 to 4 N, O and/or S atoms, which may be unsubstituted or mono-, di- or trisubstituted by carbonyl oxygen, Hal, A, —(CH$_2$)$_b$—Ar, —(CH$_2$)$_b$-cycloalkyl, OH, OA, NH$_2$, NHA, NA$_2$, NO$_2$, CN, COOH, COOA, CONH$_2$, CONHA, CONA$_2$, NHCOA, NHCONH$_2$, NHSO$_2$A, CHO, COA, SO$_2$NH$_2$ and/or S(O)$_g$A,
Hal denotes F, Cl, Br or I,
R$^4$ denotes Hal, OH, CN, NO$_2$, CF$_3$, OCF$_3$, SCF$_3$, SO$_2$A or OA,
X denotes O, S, SO$_2$NH or NH,
Y denotes phenyl or a monocyclic aromatic heterocycle having 1 to 4 N, O and/or S atoms,
b, denotes 0, 1, 2, 3 or 4,
g denotes 0, 1 or 2,
n, m, p, q each, independently of one another, denote 1, 2, 3 or 4,
and pharmaceutically acceptable salts, derivatives, solvates and stereoisomers thereof, including mixtures thereof in all ratios.

It has been found that the compounds of the formula I are capable of inhibiting, regulating and/or modulating signal transduction mediated by kinases, in particular by tyrosine kinases and/or Raf kinases. In particular, the compounds according to the invention are suitable as inhibitors of tyrosine kinases and/or Raf kinases. Thus, medicaments and pharmaceutical compositions according to the invention can be effective employed for the treatment of diseases that are caused, mediated and/or propagated by kinases and/or by kinase-mediated signal transduction or by angiogenesis. Thus, the compounds according to the invention are suitable for the treatment and prophylaxis of cancer, tumour growth, arteriosclerosis, age-induced macular degeneration, diabetic retinopathy, inflammatory diseases and the like in mammals.

Tyrosine kinases are a class of enzymes which catalyse the transfer of the terminal phosphate of adenosine triphosphate to tyrosine residues in protein substrates. It is thought that tyrosine kinases, through substrate phosphorylation, play a crucial role in signal transduction for a number of cellular functions. Although the precise mechanisms of signal transduction are still unclear, tyrosine kinases have been shown to be important factors in cell proliferation, carcinogenesis and cell differentiation.

Tyrosine kinases can be categorised as receptor-type tyrosine kinases or non-receptor-type tyrosine kinases. Receptor-type tyrosine kinases have an extracellular portion, a transmembrane portion and an intracellular portion, while non-receptor-type tyrosine kinases are exclusively intracellular.

Receptor-type tyrosine kinases consist of a multiplicity of transmembrane receptors with different biological activity. Thus, about 20 different sub-families of receptor-type tyrosine kinases have been identified. One tyrosine kinase subfamily, known as the EGFR or HER subfamily, consists of EGFR, HER2, HER3 and HER4. Ligands from this subfamily of receptors include epithelial growth factor (EGF), tissue growth factor (TGF-α), amphiregulin, HB-EGF, betacellulin and heregulin. Another subfamily of these receptor-type tyrosine kinases is the insulin subfamily, which includes INS-R, IGF-IR and IR-R. The PDGF subfamily includes the PDGF-α and -β receptor, CSFIR, c-kit and FLK-II. In addition, there is the FLK family, which consists of the kinase insert domain receptor (KDR) or VEGFR-2, foetal liver kinase-1 (FLK-1), foetal liver kinase-4 (FLK-4) and fms tyrosine kinase-1 (flt-1) or VEGFR-1. The PDGF and FLK family are usually combined in the group of the split kinase domain receptor tyrosine kinases (Laird, A. D. and J. M. Cherrington, Expert. Opin. Investig. Drugs 12(1): 51-64, 2003) due to the similarities between the two groups. For a detailed discussion of receptor-type tyrosine kinases, see the paper by Plowman et al., DN & P 7(6):334-339, 1994, which is incorporated herein by way of reference.

Non-receptor-type tyrosine kinases likewise consist of a multiplicity of subfamilies, including Src, Frk, Btk, Csk, Abl, Zap70, Fes/Fps, Fak, Jak, Ack, and LIMK. Each of these subfamilies is further sub-divided into different sub-groups. For example, the Src subfamily is one of the largest subfamilies. It includes Src, Yes, Fyn, Lyn, Lck, Blk, Hck, Fgr and Yrk. The Src subfamily of enzymes has been linked to oncogenesis. For a more detailed discussion of non-receptor-type tyrosine kinases, see the paper by Bolen, Oncogene, 8:2025-2031 (1993), which is incorporated herein by way of reference.

Both receptor-type tyrosine kinases and non-receptor-type tyrosine kinases are involved in cellular signal pathways leading to conditions such as cancer, psoriasis and hyperimmune responses.

Cancer is a disease whose causes are to be seen in disturbed signal transduction. In particular, deregulated signal transduction via tyrosine kinases plays a major role in the growth and spread of cancer (Blume-Jensen, P. and T. Hunter, Nature 411: 355-365, 2001; Hanahan D. and R. A. Weinberg, Cell 100:57-70, 2000). Tyrosine kinases and in particular receptor-type tyrosine kinases and the growth factors binding to them may thus be involved in deregulated apoptosis, tissue invasion, metastasis and generally in signal transduction mechanisms which lead to cancer.

In particular, receptor-type tyrosine kinases play a role in angiogenesis, a further important mechanism in the growth and spread of cancer (Mustonen and Alitalo, J. Cell Biol. 129:895-898,1995). One of these receptor-type tyrosine kinases is foetal liver kinase 1, also referred to as FLK-1. The human analogue of FLK-1 is the kinase insert domain-containing receptor KDR, which is also known as vascular endothelial cell growth factor receptor 2 or VEGFR-2, since it binds VEGF with high affinity. The murine version of this receptor has been called NYK (Oelrichs et al., Oncogene 8(1):11-15, 1993). VEGF and KDR are a ligand-receptor pair which plays a vital role in the proliferation of vascular endothelial cells and the formation and sprouting of blood vessels, referred to as vasculogenesis and angiogenesis respectively.

Angiogenesis is characterised by excessive activity of vascular endothelial growth factor (VEGF). VEGF actually consists of a family of ligands (Klagsburn and D'Amore, Cytokine & Growth Factor Reviews 7:259-270, 1996). VEGF binds the high-affinity membrane-spanning tyrosine kinase receptor KDR and the related fms tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF, whereas Flt-1 appears to modulate non-mitogenic functions, such as those associated with cellular adhesion. Inhibiting KDR thus modulates the level of mitogenic VEGF activity. In fact, tumour growth has been shown to be influenced by the antiangiogenic effect of VEGF receptor antagonists (Kim et al., Nature 362, pp. 841-844, 1993).

Expression of VEGF is also significantly increased in hypoxic regions of animal and human tumours adjacent to areas of necrosis. In addition, VEGF is upregulated by the expression of the on cogenes ras, raf, src and p53 mutants (all of which are of importance in combating cancer). Anti-VEGF monoclonal antibodies inhibit the growth of human tumours in nude mice. Although the same tumour cells continue to express VEGF in culture, the antibodies do not diminish their mitotic rate. Thus, tumour-derived VEGF does not function as an autocrine mitogenic factor. VEGF therefore contributes to tumour growth in vivo by promoting angiogenesis through its paracrine vascular endothelial cell chemotactic and mitogenic activity. These monoclonal antibodies also inhibit the growth of typically less well vascularised human colon carcinomas in athymic mice and decrease the number of tumours arising from inoculated cells.

Solid tumours can be treated with tyrosine kinase inhibitors since these tumours depend on angiogenesis for the formation of the blood vessels that are necessary to support their growth. These solid tumours include monocytic leukaemia, carcinoma of the brain, urogenital tract, lymphatic system, stomach, larynx and lung, including lung adenocarcinoma and small cell lung carcinoma.

Further examples of solid tumours include carcinomas in which over-expression or activation of Raf-activating oncogenes (for example K-ras, erb-B) is observed. These carcinomas include pancreatic and breast carcinoma. Inhibitors of these tyrosine kinases and/or Raf kinases are therefore suitable for the prevention and treatment of proliferative diseases caused by these enzymes.

The angiogenic activity of VEGF is not limited to tumours. VEGF is also responsible for the angiogenic activity produced in or near the retina in diabetic retinopathy. This vascular growth in the retina leads to visual degeneration culminating in blindness. Ocular VEGF mRNA and protein levels that lead to neovascularisation are further elevated by conditions such as retinal vein occlusion in primates and decreased $pO_2$ level in mice. Intraocular injections of anti-VEGF monoclonal antibodies or VEGF receptor immunofusions inhibit ocular neovascularisation in both primate and rodent models. Irrespective of the cause of induction of VEGF in human diabetic retinopathy, inhibition of ocular VEGF is suitable for treating this disease.

The expression of a VEGF-binding construct of Flk-1, Flt-1, the mouse KDR receptor homologue truncated to eliminate the cytoplasmic tyrosine kinase domains but retaining a membrane anchor, in viruses virtually stops the growth of a transplantable glioblastoma in mice, presumably by the dominant negative mechanism of heterodimer formation with membrane-spanning endothelial cell VEGF receptors. Embryonic stem cells, which normally grow as solid tumours in nude mice, do not form detectable tumours if both VEGF alleles are knocked out. Taken together, these data indicate the role of VEGF in the growth of solid tumours. Inhibition of KDR or Flt-1 is involved in pathological angiogenesis, and inhibitors of these receptors are suitable for the treatment of diseases in which angiogenesis is part of the overall pathology, for example inflammation, diabetic retinal vascularisation, as well as various forms of cancer, since tumour growth is known to be dependent on angiogenesis (Weidner et al., N. Engl. J. Med., 324, pp.1-8,1991).

The present invention is directed to compounds which are capable of regulating, modulating or inhibiting VEGFR and to the use thereof for the prevention and/or treatment of diseases in connection with unregulated or disturbed VEGFR activity. In particular, the compounds according to the invention can therefore be employed in the treatment of certain forms of cancer and in the case of diseases caused by pathological angiogenesis, such as diabetic retinopathy or inflammation.

Furthermore, compounds according to the invention can be used for the isolation and investigation of the activity or expression of VEGFR. In addition, they are particularly suitable for use in diagnostic methods for diseases in connection with unregulated or disturbed VEGFR activity.

Angiopoietin 1 (Ang1), a ligand for the endothelium-specific receptor-type tyrosine kinase TIE-2, is a novel angiogenic factor (Davis et al, Cell, 1996, 87:1161-1169; Partanen et al, Mol. Cell Biol., 12:1698-1707 (1992); U.S. Pat. Nos. 5,521,073; 5,879,672; 5,877,020; and 6,030,831). The acronym TIE stands for "tyrosine kinase with Ig and EGF homology domains". TIE is used for the identification of a class of receptor-type tyrosine kinases which are expressed exclusively in vascular endothelial cells and early haemopoietic cells. TIE receptor kinases are typically characterised by the presence of an EGF-like domain and an immunoglobulin (IG)-like domain which consists of extracellular fold units stabilised by disulfide bridge bonds between the chains (Partanen et al., Curr. Topics Microbiol. Immunol., 1999, 237: 159-172). In contrast to VEGF, which exerts its function during the early stages of vascular development, Ang1 and its receptor TIE-2 act during the later stages of vascular development, i.e. during vascular transformation (transformation relates to the formation of a vascular lumen) and maturing (Yancopoulos et al., Cell, 1998, 93:661-664; Peters, K. G., Circ. Res., 1998, 83(3):342-3; Suri et al., Cell 87,1171-1180 (1996)).

Accordingly, it would be expected that inhibition of TIE-2 should interrupt the transformation and maturing of a new vascular system initiated by angiogenesis and should thus interrupt the angiogenesis process. Furthermore, inhibition at the kinase domain binding site of VEGFR-2 would block phosphorylation of tyrosine residues and serve to interrupt initiation of angiogenesis. It must therefore be assumed that inhibition of TIE-2 and/or VEGFR-2 should prevent tumour angiogenesis and serve to slow or completely eliminate tumour growth.

Accordingly, treatment of cancer and other diseases associated with inappropriate angiogenesis could be provided with inhibitors of TIE-2 and/or VEGFR-2.

The present invention is directed to compounds which are capable of inhibiting, regulating and/or modulating TIE-2 and to the use thereof for the prevention and/or treatment of diseases in connection with unregulated or disturbed TIE-2 activity. In particular, the compounds according to the invention can therefore be employed in the treatment of certain forms of cancer and in the case of diseases caused by pathological angiogenesis, such as diabetic retinopathy or inflammation.

Furthermore, compounds according to the invention can be used for the isolation and investigation of the activity or expression of TIE-2. In addition, they are particularly suitable for use in diagnostic methods for diseases in connection with unregulated or disturbed TIE-2 activity.

The compounds according to the invention can furthermore be used in order to provide additive or synergistic effects in certain existing cancer chemotherapies and radiotherapies and/or can be used to restore the efficacy of certain existing cancer chemotherapies and radiotherapies.

The present invention furthermore relates to the compounds as inhibitors of Raf kinases. Protein phosphorylation is a fundamental process for the regulation of cellular functions. The coordinated action of both protein kinases and phosphatases controls the degrees of phosphorylation and, hence, the activity of specific target proteins. One of the predominant roles of protein phosphorylation is in signal transduction, where extracellular signals are amplified and propagated by a cascade of protein phosphorylation and dephosphorylation events, for example in the $p21^{ras}$/raf pathway.

The $p21^{ras}$ gene was discovered as an oncogene of the Harvey (H-Ras) and Kirsten (K-Ras) rat sarcoma viruses. In humans, characteristic mutations in the cellular Ras gene (c-Ras) have been associated with many different types of cancer. These mutant alleles, which render Ras constitutively active, have been shown to transform cells, such as, for example, the murine cell line NIH 3T3, in culture.

The $p21^{ras}$ oncogene is an important factor in the development and progression of human solid carcinomas and is mutated in 30% of all human carcinomas (Bolton et al. (1994) Ann. Rep. Med. Chem., 29, 165-74; Bos. (1989) Cancer Res., 49, 4682-9). In its normal, unmutated form, the Ras protein is a key element of the signal transduction cascade directed by growth factor receptors in almost all tissues (Avruch et al. (1994) Trends Biochem. Sci., 19, 279-83).

Biochemically, Ras is a guanine nucleotide binding protein, and the cycle between a GTP-bound activated and a GDP-bound resting form is strictly controlled by Ras endogenous GTPase activity and other regulatory proteins. The Ras gene product binds to guanine triphosphate (GTP) and guanine diphosphate (GDP) and hydrolyses GTP to GDP. Ras is active in the GTP-bound state. In the Ras mutants in cancer cells, the endogenous GTPase activity is reduced, and the protein consequently transmits constitutive growth signals to downstream effectors, such as, for example, the enzyme Raf kinase. This leads to the cancerous growth of the cells which carry these mutants (Magnuson et al. (1994) Semin. Cancer Biol., 5, 247-53). The Ras proto-oncogene requires a functionally intact C-Raf-1 proto-oncogene in order to transduce growth and differentiation signals initiated by receptor- and non-receptor-type tyrosine kinases in higher eukaryotes.

Activated Ras is necessary for the activation of the C-Raf-1 proto-oncogene, but the biochemical steps through which Ras activates the Raf-1 protein (Ser/Thr) kinase are now well characterised. It has been shown that inhibiting the effect of active Ras by inhibiting the Raf kinase signal pathway by administration of deactivating antibodies to Raf kinase or by co-expression of dominant negative Raf kinase or dominant negative MEK (MAPKK), the substrate of Raf kinase, leads to reversion of transformed cells and to the normal growth phenotype (see: Daum et al. (1994) Trends Biochem. Sci., 19, 474-80; Fridman et al. (1994) J Biol. Chem., 269, 30105-8; Kolch et al. (1991) Nature, 349, 426-28); review Weinstein-Oppenheimer et al. Pharm. & Therap. (2000), 88, 229-279).

Similarly, inhibition of Raf kinase (by antisense oligodeoxynucleotides) has been correlated in vitro and in vivo with inhibition of the growth of a variety of types of human tumour (Monia et al., Nat. Med. 1996, 2, 668-75).

Raf serine- and threonine-specific protein kinases are non-receptor-type enzymes that stimulate cell growth in a variety of cellular systems (Rapp, U. R., et al. (1988) in The Oncogene Handbook; T. Curran, E. P. Reddy and A. Skalka (eds.) Elsevier Science Publishers; The Netherlands, pp. 213-253; Rapp, U. R., et al. (1988) Cold Spring Harbor Sym. Quant. Biol. 53:173-184; Rapp, U. R., et al. (1990) Inv Curr. Top. Microbiol. Immunol. Potter and Melchers (eds.), Berlin, Springer-Verlag 166:129-139).

Three isozymes have been characterised:

C-Raf (Raf-1) (Bonner, T. I., et al. (1986) Nucleic Acids Res. 14:1009-1015). A-Raf (Beck, T. W., et al. (1987) Nucleic Acids Res. 15:595-609), and B-Raf (Qkawa, S., et al. (1998) Mol. Cell. Biol. 8:2651-2654; Sithanandam, G. et al. (1990) Oncogene:1775). These enzymes differ in their expression in various tissues. Raf-1 is expressed in all organs and in all cell lines that have been examined, and A- and B-Raf are expressed in urogenital and brain tissues respectively (Storm, S. M. (1990) Oncogene 5:345-351).

Raf genes are proto-oncogenes: they can initiate malignant transformation of cells when expressed in specifically altered forms. Genetic changes that lead to oncogenic activation generate a constitutively active protein kinase by removal of or interference with an N-terminal negative regulatory domain of the protein (Heidecker, G., et al. (1990) Mol. Cell. Biol. 10:2503-2512; Rapp, U. R., et al. (1987) in Oncogenes and Cancer; S. A. Aaronson, J. Bishop, T. Sugimura, M. Terada, K. Toyoshima and P. K. Vogt (eds.) Japan Scientific Press, Tokyo). Microinjection into NIH 3T3 cells of oncogenically activated, but not wild-type, versions of the Raf protein prepared with Escherichia coli expression vectors results in morphological transformation and stimulates DNA synthesis (Rapp, U. R., et al. (1987) in Oncogenes and Cancer; S. A. Aaronson, J. Bishop, T. Sugimura, M. Terada, K. Toyoshima, and P. K. Vogt (eds.) Japan Scientific Press, Tokyo; Smith, M. R., et al. (1990) Mol. Cell. Biol. 10:3828-3833).

Consequently, activated Raf-1 is an intracellular activator of cell growth. Raf-1 protein serine kinase is a candidate for the downstream effector of mitogen signal transduction, since Raf oncogenes overcome apoptosis resulting from blockage of cellular Ras activity due either to a cellular mutation (Ras revertant cells) or microinjection of anti-Ras antibodies (Rapp, U. R., et al. (1988) in The Oncogene Handbook, T. Curran, E. P. Reddy and A. Skalka (eds.), Elsevier Science Publishers; The Netherlands, pp. 213-253; Smith, M. R., et al. (1986) Nature (London) 320:540-543).

C-Raf function is required for transformation by a variety of membrane-bound oncogenes and for growth stimulation by mitogens contained in serums (Smith, M. R., et al. (1986)

Nature (London) 320:540-543). Raf-1 protein serine kinase activity is regulated by mitogens via phosphorylation (Morrison, D. K., et al. (1989) Cell 58:648-657), which also effects sub-cellular distribution (Olah, Z., et al. (1991) Exp. Brain Res. 84:403; Rapp, U. R., et al. (1988) Cold Spring Harbor Sym. Quant. Biol. 53:173-184. Raf-1-activating growth factors include platelet-derived growth factor (PDGF) (Morrison, D. K., et al. (1988) Proc. Natl. Acad. Sci. USA 85:8855-8859), colony-stimulating factor (Baccarini, M., et al. (1990) EMBO J. 9:3649-3657), insulin (Blackshear, P. J., et al. (1990) J. Biol. Chem. 265:12115-12118), epidermal growth factor (EGF) (Morrison, R. K., et al. (1988) Proc. Natl. Acad. Sci. USA 85:8855-8859), interleukin-2 (Turner, B. C., et al. (1991) Proc. NatI. Acad. Sci. USA 88:1227) and interleukin-3 and granulocyte macrophage colony-stimulating factor (Carroll, M. P., et al. (1990) J. Biol. Chem. 265:19812-19817).

After mitogen treatment of cells, the transiently activated Raf-1 protein serine kinase translocates to the perinuclear area and the nucleus (Olah, Z., et al. (1991) Exp. Brain Res. 84:403; Rapp, U. R., et al. (1988) Cold Spring Habor Sym. Quant. Biol. 53:173-184). Cells containing activated Raf are altered in their pattern of gene expression (Heidecker, G., et al. (1989) in Genes and signal transduction in multistage carcinogenesis, N. Colburn (ed.), Marcel Dekker, Inc., New York, pp. 339-374) and Raf-oncogenes activate transcription from Ap-I/PEA3-dependent promoters in transient transfection assays (Jamal, S., et al. (1990) Science 344:463-466; Kaibuchi, K., et al. (1989) J. Biol. Chem. 264:20855-20858; Wasylyk, C., et al. (1989) Mol. Cell. Biol. 9:2247-2250).

There are at least two independent pathways for Raf-1 activation by extracellular mitogens: one involving protein kinase C (KC) and a second initiated by protein tyrosine kinases (Blackshear, P. J., et al. (1990) J. Biol. Chem. 265: 12131-12134; Kovacina, K. S., et al. (1990) J. Biol. Chem. 265:12115-12118; Morrison, D. K., et al. (1988) Proc. Natl. Acad. Sci. USA 85:8855-8859; Siegel, J. N., et al. (1990) J. Biol. Chem. 265:18472-18480; Turner, B. C., et al. (1991) Proc. Natl. Acad. Sci. USA 88:1227). In each case, activation involves Raf-1 protein phosphorylation. Raf-1 phosphorylation may be a consequence of a kinase cascade amplified by autophosphorylation or may be caused entirely by autophosphorylation initiated by binding of a potential activating ligand to the Raf-1 regulatory domain, analogous to PKC activation by diacylglycerol (Nishizuka, Y. (1986) Science 233:305-312).

The present invention is directed to compounds which are capable of inhibiting, regulating and/or modulating Raf kinases and to the use thereof for the prevention and/or treatment of diseases in connection with unregulated or disturbed Raf kinase activity. In particular, the compounds according to the invention can therefore be employed in the treatment of certain forms of cancer. As already mentioned above, the compounds according to the invention can be used in order to provide additive or synergistic effects in certain existing cancer chemotherapies and radiotherapies and/or can be used to restore the efficacy of certain existing cancer chemotherapies and radiotherapies.

Furthermore, compounds according to the invention can be used for the isolation and investigation of the activity or expression of Raf kinases. In addition, they are particularly suitable for use in diagnostic methods for diseases in connection with unregulated or disturbed Raf kinase activity.

One of the principal mechanisms by which cellular regulation is effected is the transduction of extracellular signals across the membrane that in turn modulate biochemical pathways within the cell. Protein phosphorylation represents one course by which intracellular signals are propagated from molecule to molecule resulting finally in a cellular response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a ubiquitous process within cells and since cellular phenotypes are largely influenced by the activity of these pathways, it is currently believed that a large number of disease states and/or diseases are attributable to either aberrant activation or functional mutations in the molecular components of kinase cascades. Consequently, considerable attention has been devoted to the characterisation of these proteins and compounds that are able to modulate their activity (for review see: Weinstein-Oppenheimer et al. Pharma. &. Therap., 2000, 88, 229-279). Various possibilities for the inhibition, regulation and modulation of kinases encompass, for example, the provision of antibodies, antisense ribozymes and inhibitors. In oncology research, tyrosine kinases, in particular, are highly promising targets. Thus, numerous synthetic small molecules are undergoing clinical development as tyrosine kinase inhibitors for the treatment of cancer, for example Iressa® or Gleevec®. However, numerous problems, such as side effects, dosage, resistance of the tumour, tumour specificity and patient selection, still have to be solved here.

WO 02/44156 describes benzimidazole derivatives as TIE-2 and/or VEGFR2 inhibitors. WO 99/32436, WO 02/062763 WO 99/32455, WO 00/42012 and WO 02/085857 disclose urea derivatives as Raf kinase inhibitors.

The invention was based on the object of finding novel compounds having valuable properties, in particular those which can be used for the preparation of medicaments.

The identification and provision of small compounds which specifically inhibit, regulate and/or modulate signal transduction of tyrosine kinases and/or Raf kinases is therefore desirable and an aim of the present invention.

It has been found that the compounds according to the invention and salts thereof have very valuable pharmacological properties while being well tolerated.

In particular, it has been found that the compounds according to the invention surprisingly are effective kinase inhibitors.

Thus, they exhibit a tyrosine kinase-inhibiting action, in particular a TIE-2- and/or VEGFR-inhibiting action. Furthermore, according to the invention are effective inhibitors of Raf kinases.

SUMMARY OF THE INVENTION

The invention relates to the above-mentioned compounds of the formula I.

Throughout the invention, all radicals which occur more than once may be identical or different, i.e. are independent of one another. Above and below, the radicals and parameters have the meanings indicated for the formula I, unless expressly stated otherwise. Accordingly, the invention relates, in particular, to the compounds of the formula I in which at least one of the said radicals has one of the preferred meanings indicated below.

Hal denotes fluorine, chlorine, bromine or iodine, in particular fluorine or chlorine.

A denotes alkyl, is unbranched (linear), branched or cyclic, and has 1, 2, 3, 4, 5, 6, 7, 8, 9, 10, 11, 12, 13 or 14 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, linear or branched heptyl, octyl, nonyl or decyl.

A very particularly preferably denotes alkyl having 1, 2, 3, 4, 5 or 6 C atoms, in which one or two $CH_2$ groups may be replaced by O or S atoms and/or by —CH=CH— groups and/or in addition 1-7 H atoms may be replaced by F and/or Cl, such as, for example, methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cycloalkyl preferably denotes cyclopropyl, cyclobutyl, cyclopentyl, cyclohexyl or cycloheptyl.

OA is preferably methoxy, furthermore also ethoxy, n-propoxy, isopropoxy, n-butoxy, isobutoxy, sec-butoxy or tert-butoxy.

Ar denotes, for example, unsubstituted phenyl, naphthyl or biphenyl, furthermore preferably phenyl, naphthyl or biphenyl which is mono-, di- or trisubstituted by, for example, A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, aminocarbonyl.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butyl-phenyl, o-, m- or p-hydroxyphenyl, o-, m- or p-nitrophenyl, o-, m- or p-aminophenyl, o-, m- or p-(N-methylamino)phenyl, o-, m- or p-(N-methyl-aminocarbonyl)phenyl, o-, m- or p-acetamidophenyl, o-, m- or p-methoxy-phenyl, o-, m- or p-ethoxyphenyl, o-, m- or p-ethoxycarbonylphenyl, o-, m- or p-(N,N-dimethylamino) phenyl, o-, m- or p-(N,N-dimethylaminocarbonyl)-phenyl, o-, m- or p-(N-ethylamino)phenyl, o-, m- or p-(N,N-diethylamino)-phenyl, o-, m- or p-fluorophenyl, o-, m- or p-bromophenyl, o-, m- or p-chlorophenyl, o-, m- or p-(methylsulfonamido)phenyl, o-, m- or p-(methyl-sulfonyl)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Het preferably denotes 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1 ,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzo-dioxol-5-yl, 1,4-benzodioxan-6-yl, 2,1,3-benzothiadiazol-4- or -5-yl or 2,1,3-benzoxadiazol-5-yl, each of which is unsubstituted or mono-, di- or trisubstituted by, for example, carbonyl oxygen, F, Cl, Br, methyl, ethyl, propyl, phenyl, benzyl, -$CH_2$-cyclohexyl, hydroxyl, methoxy, ethoxy, amino, methylamino, dimethylamino, nitro, cyano, carboxyl, methoxycarbonyl, aminocarbonyl, methylaminocarbonyl, dimethylaminocarbonyl, acetamino, ureido, methylsulfonylamino, formyl, acetyl, aminosulfonyl and/or methylsulfonyl.

The heterocyclic radicals may also be partially or fully hydrogenated and also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-,-2-,-3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Het furthermore denotes, for example, 2-oxopiperidin-1-yl, 2-oxopyrrolidin-1-yl, 2-oxo-1H-pyridin-1-yl, 3-oxomorpholin-4-yl, 4-oxo-1 H-pyridin-1-yl, 2,6-dioxopiperidin1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-hydroxy-6-oxopiperazin-1-yl, 2-methoxy-6-oxopiperazin-1-yl or 2-azabicyclo[2.2.2]octan-3-on-2-yl.

$R^1$ preferably denotes H, Hal, $CF_3$, $NO_2$, COOH or COOR. $R^2$ preferably denotes H. $R^3$ preferably denotes H, Hal or CO-NHR. R preferably denotes H or unsubstituted or mono-, di-, tri- or tetra-$R^4$-substituted A, Ar, Het, $(CH_2)_q$Het or $(CH_2)_q$Ar. $R^4$ preferably denotes Hal, OH, CN, $NO_2$, $CF_3$, $OCF_3$, $SCF_3$, $SO_2A$ or OA.

Ⓨ preferably denotes phenyl or a monocyclic aromatic heterocycle having 1 to 4 N, O and/or S atoms, Ⓨ particularly preferably denotes phenyl, furyl, thienyl, pyrrolyl, imidazolyl, pyridyl or pyrimidinyl, Ⓨ very particularly preferably denotes phenyl, pyridyl or pyrimidinyl. X preferably denotes O, S, $SO_2NH$ or NH.

The terms "group", "residue", "radical" or "groups", "residues", "radicals" are used synonymously here, as is usual in the art.

The term "substituted" preferably refers to substitution by the above-mentioned substituents, with a plurality of different degrees of substitution being possible, unless specified otherwise.

All physiologically acceptable salts, derivatives, solvates and stereoisomers of these compounds, including mixtures thereof in all ratios, are also in accordance with the invention.

The compounds of the formula I can have one or more chiral centres. Accordingly, they can occur in various enantiomeric forms and exist in racemic or in optically active form. The invention therefore also relates to the optically active forms (stereoisomers), the enantiomers, the racemates, the diastereomers and hydrates and solvates of these compounds.

Since the pharmaceutical efficacy of the racemates or stereoisomers of the compounds according to the invention may differ, it may be desirable to use the enantiomers. In these cases, the end product or alternatively already the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Suitable resolving agents are, for example, optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline) or the various optically active camphorsulfonic acids. Chromatographic enantiomer resolution with the aid of an optically active resolving agent (for example dinitrobenzoylphenyl-glycine, cellulose triacetate or other derivatives of carbohydrates or chirally derivatised methacrylate polymers immobilised on silica gel) is also advantageous. Suitable eluents for this purpose are aqueous or alcoholic solvent mixtures, such as, for example, hexane/isopropanol/acetonitrile, for example in the ratio 82:15:3.

Some preferred groups of compounds can be expressed by the following sub-formulae Ia to Ie, which conform to the formula I and in which the radicals not designated in greater detail have the meaning indicated for the formula I, but in which in Ia $R^1$ denotes Hal, $NO_2$, $CF_3$, COOH, COOR or H,
in Ib $R^2$ denotes H,
in Ic $R^3$ denotes H, Hal or CO—NHR,
in Id Y denotes phenyl, furyl, thienyl, pyrrolyl, imidazolyl, pyridyl or pyrimidinyl,
in Ie $R^1$ denotes Hal, $NO_2$, $CF_3$, COOH, COOR or H,
  $R^2$ denotes H,
  $R^3$ denotes H, Hal or CO—NHR,
  Y denotes phenyl, furyl, thienyl, pyrrolyl, imidazolyl, pyridyl or pyrimidinyl,
  X denotes O, S, $SO_2NH$ or NH,
  n, p, independently of one another, denote 1, 2, 3 or 4,
  m denotes 1,
and pharmaceutically acceptable salts, derivatives, solvates and stereoisomers thereof, including mixtures thereof in all ratios.

The compounds are particularly preferably selected from the group
a) benzoxazol-2-yl-[4-(pyridin-4-yloxy)phenyl]amine,
b) benzoxazol-2-yl-[4-(pyridin-4-ylsulfanyl)phenyl]amine,
c) N-benzoxazol-2-yl-N'-pyridin-4-ylbenzene-1,4-diamine,
d) 2-[4-(pyridin-4-ylsulfanyl)phenylamino]benzoxazole-5-carboxylic acid,
e) 2-[4-(pyridin-4-yloxy)phenylamino]benzoxazole-6-carboxylic acid,
f) 2-[4-(pyridin-4-ylsulfanyl)phenylamino]benzoxazole-6-carboxylic acid,
g) methyl 2-[4-(pyridin-4-ylamino)phenylamino]benzoxazole-6-carboxylate,
h) (5-nitrobenzoxazol-2-yl)-[4-(pyridin-4-ylsulfanyl)phenyl]amine,
i) (5-nitrobenzoxazol-2-yl)-[4-(pyridin-4-yloxy)phenyl]amine,
j) N-(5-nitrobenzoxazol-2-yl)-N'-pyridin-4-ylbenzene-1,4-diamine,
k) (6-nitrobenzoxazol-2-yl)-[4-(pyridin-4-yloxy)phenyl]amine,
l) (6-nitrobenzoxazol-2-yl)-[4-(pyridin-4-ylsulfanyl)phenyl]amine,
m) N-(6-nitrobenzoxazol-2-yl)-N'-pyridin-4-ylbenzene-1,4-diamine,
n) (5-chloro-7-nitrobenzoxazol-2-yl)-[4-(pyridin-4-yloxy)phenyl]amine,
o) (5-chloro-7-nitrobenzoxazol-2-yl)-[4-(pyridin-4-ylsulfanyl)phenyl]amine,
p) N-(5-chloro-7-nitrobenzoxazol-2-yl)-N'-pyridin-4-ylbenzene-1,4-diamine,
q) (7-bromo-5-trifluoromethylbenzoxazol-2-yl)-[4-(pyridin-4-yloxy)phenyl]-amine,
r) (7-bromo-5-trifluoromethylbenzoxazol-2-yl)-[4-(pyridin-4-ylsulfanyl)-phenyl]amine,
s) (7-bromo-5-trifluoromethylbenzoxazol-2-yl)-[4-(4-fluorophenylsulfanyl)-phenyl]amine,
t) N-[4-(bromotrifluoromethylbenzoxazol-2-ylamino)phenyl]-4-fluorobenzenesulfonamide,
u) [4-(2-amino-6-methylpyrimidin-4-yloxy)phenyl]-(7-bromo-5-trifluoromethylbenzoxazol-2-yl)amine,
v) N-methyl-4-[4-(bromotrifluoromethylbenzoxazol-2-ylamino)phenoxy]-pyridine-2-carboxamide,
w) N-methyl-4-[4-(bromotrifluoromethylbenzoxazol-2-ylamino)phenylsulfanyl]pyridine-2-carboxamide,
x) (7-bromo-5-trifluoromethylbenzoxazol-2-yl)-[4-(2,4-difluorophenylsulfanyl)phenyl]amine,
and pharmaceutically acceptable salts, derivatives, solvates and stereoisomers thereof, including mixtures thereof in all ratios.

Pharmaceutically or physiologically acceptable derivatives is taken to mean, for example, salts of the compounds according to the invention and also so-called prodrug compounds. Such derivatives are known in the person skilled in the art. A review of physiologically tolerated derivatives is given in Burger's Medicinal Chemistry And Drug Discovery, 5th Edition, Vol 1: Principles and Practice. Prodrug compounds is taken to mean compounds of the formula I which have been modified with, for example, alkyl or acyl groups, sugars or oligopeptides and which are rapidly cleaved or liberated in the organism to give the effective compounds according to the invention. These also include biodegradable polymer derivatives of the compounds according to the invention, as described, for example, in Int. J. Pharm. 115 (1995), 61-67.

Suitable acid-addition salts are inorganic or organic salts of all physiologically or pharmacologically acceptable acids, for example halides, in particular hydrochlorides or hydrobromides, lactates, sulfates, citrates, tartrates, maleates, fumarates, oxalates, acetates, phosphates, methylsulfonates or p-toluenesulfonates.

Solvates of the compounds of the formula I is taken to mean adductions of inert solvent molecules onto the compounds of the formula I which form owing to their mutual attractive force. Solvates are, for example, hydrates, such as monohydrates or dihydrates, or alcoholates, i.e. addition compounds with alcohols, such as, for example, with methanol or ethanol.

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence: improved treatment, healing, prevention or elimination of a disease, syndrome, disease state, condition, disorder or prevention of side effects or also reduction in the progress of a disease, condition or disorder. The expression "therapeutically effective amount" also encompasses the amounts which are effective for increasing normal physiological function.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

Process for the preparation of compounds of the formula I and physiologically acceptable salts, derivatives, solvates and stereoisomers thereof, characterised in that a compound of the formula II

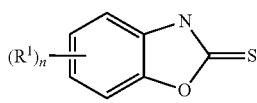

II in which $R^1$ and n have the above-mentioned meanings, is reacted with a compound of the formula III

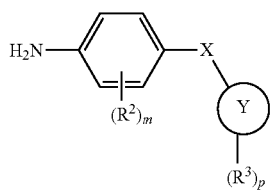

III in which $R^2$, $R^3$, X, Y, m and p have the above-mentioned meanings, and/or a base or acid of the formula I is converted into one of its salts.

The preparation of the compounds of the formula I can also be represented by the following scheme.

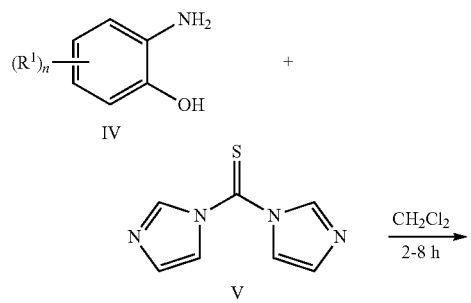

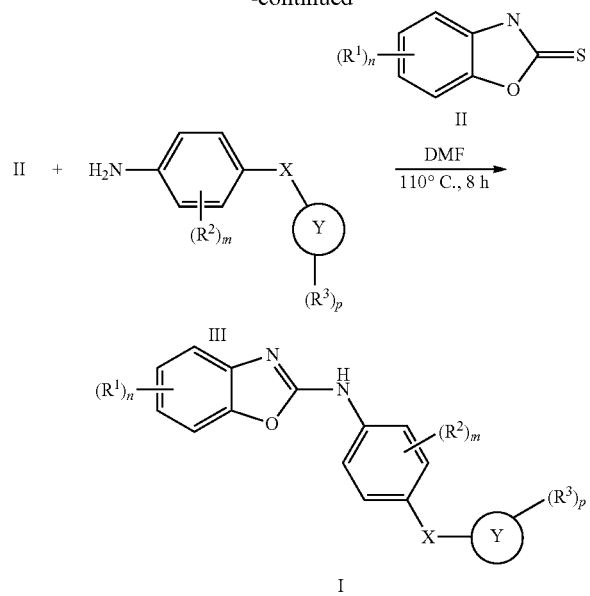

The compounds of the formula IV and V are particularly preferably converted into a compound of the formula II overnight at room temperature in the presence of the solvents dichloromethane and dimethylformamide. The compounds of the formula II and III are particularly preferably converted into a compound of the formula I overnight at 110° C. in the presence of dimethylformamide.

It is also possible to carry out each of the reactions stepwise.

The starting compounds are generally known. If they are novel, they can be prepared by methods known per se.

The starting materials can, if desired, also be formed in situ so that they are not isolated from the reaction mixture, but instead are immediately converted further into the compounds of the formula I.

The starting materials can be combined (melted) in a sealed reaction vessel or autoclave in the absence of a solvent. However, it is also possible to allow the starting materials to react in the presence of an inert solvent.

The reaction of the compounds of the formula II and III is carried out by methods which are known to the person skilled in the art. The reaction is firstly carried out in a suitable solvent, in particular in an inert solvent.

Suitable inert solvents are, for example, heptane, hexane, petroleum ether, benzene, toluene, xylene, trichloroethylene, 1,2-dichloroethanetetrachloromethane, chloroform or dichloromethane; alcohols, such as methanol, ethanol, isopropanol, n-propanol, n-butanol or tert-butanol; ethers, such as diethyl ether, diisopropyl ether (preferred for substitution on the indole nitrogen), tetrahydrofuran (THF) or dioxane; glycol ethers, such as ethylene glycol monomethyl or monoethyl ether (methyl glycol or ethyl glycol), ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; esters, such as ethyl acetate, carboxylic acids or acid anhydrides, such as, for example, such as acetic acid or acetic anhydride, nitro compounds, such as nitromethane or nitrobenzene, if desired also mixtures of the said solvents with one another or mixtures with water. Particular preference is given to dimethylformamide.

The reaction can also be carried out in heterogeneous phase, preferably using an aqueous phase and a benzene or toluene phase. Use is made here of a phase-transfer catalyst, such as, for example, tetrabutylammonium iodide, and optionally an acylation catalyst, such as, for example, dimethylaminopyridine.

The amount of solvent is not crucial, preferably 10 g to 500 g of solvent can be added per g of the compound of the formula I to be reacted.

Suitable reaction temperatures are at temperatures of 10 to 180° C., preferably at 20 to 150° C. and very particularly preferably at 60 to 120° C.

The reaction is preferably carried out at a pressure of 1 to 200 bar, particularly preferably at atmospheric pressure.

The reaction is preferably carried out at a pH of 4 to 10.

The duration of the reaction depends on the reaction conditions selected. In general, the reaction duration is 0.5 hours to 10 days, preferably 1 to 24 hours, particularly preferably 2 to 12 hours.

The compounds of the formula I and also the starting materials for their preparation are, in addition, prepared by known methods, as described in the literature (for example in standard works, such as Houben-Weyl, Methoden der organischen Chemie [Methods of Organic Chemistry], Georg-Thieme-Verlag, Stuttgart), for example under reaction conditions which are known and suitable for the said reactions. Use can also be made here of variants known per se which are not described here in greater detail.

After removal of the solvent, the compounds of the formula I can be obtained by conventional work-up steps, such as, for example, addition of water to the reaction mixture and extraction. It may be advantageous subsequently to carry out a distillation or crystallisation for further purification of the product.

The conversion of compounds of the formula IV and V into compounds of the formula II is carried out by processes indicated above. The inert solvents used are particularly preferably dichloromethane and dimethylformamide. The process is preferably carried out at temperatures of 10 to 40 degrees, particularly preferably at room temperature, and atmospheric pressure. The reaction duration is particularly preferably 2 to 12 hours.

An acid of the formula I can be converted into the associated addition salt using a base, for example by reaction of equivalent amounts of the acid and base in an inert solvent, such as ethanol, and included evaporation. Particularly suitable bases for this reaction are those which give physiologically acceptable salts. Thus, the acid of the formula I can be converted into the corresponding metal salt, in particular alkali or alkaline earth metal salt, or into the corresponding ammonium salt using a base (for example sodium hydroxide or carbonate or potassium hydroxide or carbonate). Suitable for this reaction are also organic bases which give physiologically acceptable salts, such as, for example, ethanolamine.

On the other hand, a base of the formula I can be converted into the associated acid-addition salt using an acid, for example by reaction of equivalent amounts of the base and acid in an inert solvent, such as ethanol, followed by evaporation. Particularly suitable acids for this reaction are those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic, mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxysulfonic acid, benzenesulfonic acid, p-toluenesulfonic acid, naphthalenemono- and disulfonic acids or laurylsulfuric acid. Salts with physiologically unacceptable acids, for example picrates, can be used for the isolation and/or purification of the compounds of the formula I.

The invention furthermore relates to medicaments comprising at least one compound according to the invention and/or physiologically acceptable salts, derivatives, solvates and stereoisomers thereof, including mixtures thereof in all ratios.

A pharmaceutical composition according to the invention may furthermore comprise further excipients and/or adjuvants and optionally one or more further medicament active ingredients.

The invention furthermore relates to a process for the preparation of a medicament, characterised in that a compound according to the invention and/or one of its physiologically acceptable salts, derivatives, solvates and stereoisomers, including mixtures thereof in all ratios, is brought into a suitable dosage form together with a solid, liquid or semi-liquid excipient or adjuvant.

The invention also relates to a set (kit) consisting of separate packs of (a) an effective amount of a compound according to the invention and/or physiologically acceptable salts, derivatives, solvates and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Medicaments can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient. Preferred dosage unit formulations are those which comprise a daily dose or part-dose, as indicated above, or a corresponding fraction thereof of an active ingredient. Furthermore, medicaments of this type can be prepared using a process which is generally known in the pharmaceutical art.

Medicaments can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such medicaments can be prepared using all processes known in the pharmaceutical art by, for example, combining the active ingredient with the excipient(s) or adjuvant(s).

Medicaments adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds.

The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil, or natural sweeteners or saccharin or other artificial sweeteners, and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Medicaments adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Medicaments adapted for topical administration can be formulated as ointments, creams, suspensions, lotions, powders, solutions, pastes, gels, sprays, aerosols or oils.

For treatments of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Medicaments adapted for topical application to the eye include eye drops, in which the active ingredient is dissolved or suspended in a suitable carrier, in particular an aqueous solvent.

Medicaments adapted for topical application in the mouth encompass lozenges, pastilles and mouthwashes.

Medicaments adapted for rectal administration can be administered in the form of suppositories or enemas.

Medicaments adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Medicaments adapted for administration by inhalation encompass finely particulate dusts or mists, which can be generated by various types of pressurised dispensers with aerosols, nebulisers or insufflators.

Medicaments adapted for vaginal administration can be administered as pessaries, tampons, creams, gels, pastes, foams or spray formulations.

Medicaments adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the medicaments according to the invention may also comprise other agents usual in the art with respect to the particular type of pharmaceutical formulation; thus, for example, medicaments which are suitable for oral administration may comprise flavours.

A therapeutically effective amount of a compound of the present invention depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as a fraction of the effective amount of the compound according to the invention per se. It can be assumed that similar doses are suitable for the treatment of the other conditions mentioned above.

Use

The compounds according to the invention preferably exhibit an advantageous biological activity which can easily be detected in enzyme assays, as described in the examples. In such enzyme-based assays, the compounds according to the invention preferably exhibit and cause an inhibiting effect, which is usually documented by $IC_{50}$ values in a suitable range, preferably in the micromolar range and more preferably in the nanomolar range.

The present invention relates to compounds according to the invention as activators or inhibitors, preferably as inhibitors of the signal pathways described herein. The invention therefore particularly preferably relates to compounds according to the invention as activators and inhibitors of kinases, particularly preferably as inhibitors of tyrosine kinases, in particular TIE-2 and/or VEGFR, and/or as inhibitors of Raf kinases, in particular ticular A-Raf, B-Raf and C-Raf-1.

As discussed above, the signal pathways influenced by the compounds according to the invention are relevant for various diseases. Accordingly, the compounds according to the invention are useful in the prophylaxis and/or treatment of diseases which are dependent on the said signal pathways through interaction with one or more of the said signal pathways.

The present invention therefore furthermore relates to the use of compounds according to the invention and/or physiologically acceptable salts, derivatives, solvates and stereoisomers thereof, including mixtures thereof in all ratios, for the preparation of a medicament for the treatment and/or prophylaxis of diseases, in particular diseases that are caused, mediated and/or propagated by kinases and/or by kinase-mediated signal transduction. Preference is given here to kinases selected from the group of the tyrosine kinases. The tyrosine kinases are particularly preferably TIE-2 or VEGFR. Preference is also given to kinases selected from the group of the Raf kinases. The Raf kinases are particularly preferably A-Raf, B-Raf or Raf-1.

It has been found that the compounds according to the invention are inhibitors of the enzyme Raf kinase. Since the enzyme is a downstream effector of $p21^{ras}$, the inhibitors prove to be suitable in pharmaceutical compositions for use in human or veterinary medicine where inhibition of the Raf kinase pathway is indicated, for example in the treatment of tumours and/or cancerous cell growth mediated by Raf kinase. In particular, the compounds are suitable in the treatment of human and animal solid cancers, for example murine cancer, since the progression of these types of tumour is dependent upon the Ras protein signal transduction cascade and therefore responsive to treatment by interruption of the cascade, i.e. by inhibiting Raf kinase. Accordingly, the compound according to the invention or a pharmaceutically acceptable salt thereof is administered for the treatment of diseases mediated by the Raf kinase pathway, especially cancer, including solid cancers, such as, for example, carcinomas (for example of the lungs, pancreas, thyroid, bladder or colon), myeloid diseases (for example myeloid leukaemia) or adenomas (for example villous colon adenoma), pathological angiogenesis and metastatic cell migration. The compounds are furthermore suitable in the treatment of complement activation dependent chronic inflammation (Niculescu et al. (2002) Immunol. Res., 24:191-199) and HIV-1 (human immunodeficiency virus type 1) induced immunodeficiency (Popik et al. (1998) J Virol, 72: 6406-6413).

In addition, the present compounds are suitable as pharmaceutical active ingredients for mammals, in particular for humans, in the treatment of tyrosine kinase-induced diseases. The expression "tyrosine kinase-induced diseases" refers to pathological conditions that depend on the activity of one or more tyrosine kinases. Tyrosine kinases either directly or indirectly participate in the signal transduction pathways of a variety of cellular activities, including proliferation, adhesion and migration and differentiation. Diseases associated with tyrosine kinase activity include proliferation of tumour cells, pathological neovascularisation that promotes the growth of solid tumours, ocular neovascularisation (diabetic retinopathy, age-induced macular degeneration and the like) and inflammation (psoriasis, rheumatoid arthritis and the like).

The diseases discussed herein are usually divided into two groups, hyperproliferative and non-hyperproliferative diseases. In this connection, psoriasis, arthritis, inflammation, endometriosis, scarring, benign prostatic hyperplasia, immunological diseases, autoimmune diseases and immunodeficiency diseases are regarded as non-cancerous diseases, of which arthritis, inflammation, immunological diseases, autoimmune diseases and immunodeficiency diseases are usually regarded as non-hyperproliferative diseases.

In this connection, brain cancer, lung cancer, squamous cell cancer, bladder cancer, gastric cancer, pancreatic cancer, hepatic cancer, renal cancer, colorectal cancer, breast cancer, head cancer, neck cancer, oesophageal cancer, gynaecological cancer, thyroid cancer, lymphoma, chronic leukaemia and acute leukaemia are to be regarded as cancerous diseases, all of which are usually counted in the group of hyperproliferative diseases. Especially cancerous cell growth and especially cancerous cell growth mediated directly or indirectly by TIE-2, VEGFR and Raf kinase is a disease which is a target of the present invention.

The present invention therefore relates to the use of compounds according to the invention for the preparation of a medicament for the treatment and/or prophylaxis of the said diseases and also to a method for the treatment of the said diseases which comprises the administration of one or more compounds according to the invention to a patient in need of such an administration.

It can be shown that the compounds according to the invention have an antiproliferative action in vivo in a xenotransplant tumour model. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treat" is used to refer to both prevention of diseases and treatment of pre-existing conditions. The prevention of proliferation is achieved by administration of the compounds according to the invention prior to the development of overt disease, for example to prevent tumour growth, prevent metastatic growth, diminish restenosis associated with cardiovascular surgery, etc. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The responsiveness of a particular cell to treatment with the compounds according to the invention can be determined by in-vitro tests. Typically, a culture of the cell is incubated with a compound according to the invention at various concentrations for a period of time which is sufficient to allow the active ingredients to induce cell death or to inhibit migration, usually between about one hour and one week. In-vitro tests can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the specific cell count, and may be continued until essentially no more undesired cells are detected in the body.

For the identification of kinase inhibitors, various assay systems are available. In scintillation proximity assay (Sorg et al., J. of Biomolecular Screening, 2002, 7,11-19) and flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002,191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J., just about to be published, manuscript BJ20020786).

There are many diseases and conditions associated with deregulation of cell proliferation and cell death (apoptosis). However, the diseases and conditions that can be treated, prevented or ameliorated by compounds according to the invention include, but are not limited to, the diseases and conditions listed below. The compounds according to the invention are suitable in the treatment and/or prophylaxis of a number of different diseases and conditions where there is proliferation and/or migration of smooth muscle cells and/or inflammatory cells into the intimal layer of a vessel, resulting in restricted blood flow through that vessel, for example in the case of neointimal occlusive lesions. Occlusive transplant vascular diseases of interest include atherosclerosis, coronary vascular disease after transplantation, vein graft stenosis, peri-anastomotic prosthetic restenosis, restenosis after angioplasty or stent placement, and the like.

The present invention encompasses the use of the compounds according to the invention for the treatment or prevention of cancer. In particular, the invention relates to the use of compounds according to the invention and/or physiologically acceptable salts, derivatives, solvates and stereoisomers thereof, including mixtures thereof in all ratios, for the preparation of a medicament for the treatment and/or prophylaxis of solid tumours, where the solid tumour is particularly preferably selected from the group consisting of brain tumour, tumour of the urogenital tract, tumour of the lymphatic system, stomach tumour, laryngeal tumour, lung tumour. Solid tumours selected from the group consisting of monocytic leukaemia, lung adenocarcinoma, small cell lung carcinomas, pancreatic cancer, glioblastomas and breast carcinoma can preferably also be treated with medicaments comprising compounds according to the invention.

The compounds according to the invention can be administered to patients for the treatment of cancer. The present compounds inhibit tumour angiogenesis, thereby affecting the growth of tumours (J. Rak et al. Cancer Research, 55:4575-4580, 1995). The angiogenesis-inhibiting properties of the compounds according to the invention are also suitable for the treatment of certain forms of blindness related to retinal neovascularisation.

The invention therefore also relates to the use of compounds according to the invention and/or physiologically acceptable salts, derivatives, solvates and stereoisomers thereof, including mixtures thereof in all ratios, for the preparation of a medicament for the treatment and or prophylaxis of diseases that are caused, mediated and/or propagated by angiogenesis.

Such a disease in which angiogenesis is implicated is an ocular disease, such as retinal vascularisation, diabetic retinopathy, age-induced macular degeneration and the like.

The invention therefore also relates to the use of the compounds according to the invention for the preparation of a medicament for the treatment and/or prophylaxis of the above diseases.

The use of compounds according to the invention and/or physiologically acceptable salts and solvates thereof for the preparation of a medicament for the treatment and/or prophylaxis of inflammatory diseases also falls within the scope of the present invention. Examples of such inflammatory diseases include rheumatoid arthritis, psoriasis, contact dermatitis, delayed hypersensitivity reaction and the like.

The compounds according to the invention are also suitable for the treatment of certain bone pathologies, such as osteosarcoma, osteoarthritis and rickets, also known as oncogenic osteomalacia (Hasegawa et al., Skeletal Radiol. 28, pp.41-45, 1999; Gerber et al., Nature Medicine, Vol. 5, No. 6, pp.623-628, June 1999). Since VEGF directly promotes osteoclastic bone resorption through KDR/Flk-1 expressed in mature osteoclasts (FEBS Let. 473:161-164 (2000); Endocrinology, 141:1667 (2000)), the present compounds are also suitable for the treatment and prevention of conditions related to bone resorption, such as osteoporosis and Paget's disease.

The invention therefore furthermore relates to the use of compounds according to the invention and/or physiologically acceptable salts, derivatives, solvates and stereoisomers thereof, including mixtures thereof in all ratios, for the preparation of a medicament for the treatment of bone pathologies selected from the group consisting of osteosarcoma, osteoarthritis and rickets.

The compounds can also be used for the reduction or prevention of tissue damage which occurs after cerebral ischaemic events, such as strokes, by reducing cerebral oedema, tissue damage and ischaemia-induced reperfusion injuries (Drug News Perspect 11:265-270 (1998); J. Clin. Invest. 104:1613-1620 (1999)).

The compounds according to the invention are also suitable for the preparation of a medicament for the treatment and prophylaxis of diseases that are caused, mediated and/or propagated by Raf kinases, where the Raf kinase is selected from the group consisting of A-Raf, B-Raf and Raf-1.

Preference is given to the use for the treatment of diseases, preferably from the group of hyperproliferative and non-hyperproliferative diseases. These are cancerous diseases or non-cancerous diseases.

The invention also relates to the use of compounds according to the invention and/or physiologically acceptable salts, derivatives, solvates and stereoisomers thereof, including mixtures thereof in all ratios, for the preparation of a medicament for the treatment of diseases selected from the group of non-cancerous diseases consisting of psoriasis, arthritis, inflammation, endometriosis, scarring, benign prostatic hyperplasia, immunological diseases, autoimmune diseases and immunodeficiency diseases.

The invention furthermore relates to the use of compounds according to the invention and/or physiologically acceptable salts, derivatives, solvates and stereoisomers thereof, including mixtures thereof in all ratios, for the preparation of a medicament for the treatment of diseases selected from the group of cancerous diseases consisting of brain cancer, lung cancer, squamous cell cancer, bladder cancer, gastric cancer, pancreatic cancer, hepatic cancer, renal cancer, colorectal cancer, breast cancer, head cancer, neck cancer, oesophageal cancer, gynaecological cancer, thyroid cancer, lymphoma, chronic leukaemia and acute leukaemia.

The compounds according to the invention may also be administered at the same time as other well-known therapeutic agents that are selected for their particular usefulness against the condition that is being treated. For example, in the case of bone conditions, combinations that would be favourable include those with antiresorptive bisphosphonates, such as alendronate and risedronate, integrin blockers (as defined further below), such as $\alpha v\beta 3$ antagonists, conjugated oestrogens used in hormone replacement therapy, such as Prempro®, Premarin® and Endometrion®; selective oestrogen receptor modulators (SERMs), such as raloxifene, droloxifene, CP-336,156 (Pfizer) and lasofoxifene, cathepsin K inhibitors, and ATP proton pump inhibitors.

The present compounds are also suitable for combination with known anti-cancer cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, growth factor inhibitors and angiogenesis inhibitors. The present compounds are particularly suitable for administration at the same time as radiotherapy. The synergistic effects of inhibiting VEGF in combination with radiotherapy have been described in the art (see WO 00/61186).

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperid-inyl)ethoxy]phenyl]-2H-1-benzopyran-3-yl]phenyl 2,2-dimethylpropanoate, 4,4'-dihydroxybenzophenone-2,4-dinitrophenylhydrazone and SH646. "Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenyl retinamide.

"Cytotoxic agents" refers to compounds which result in cell death primarily through direct action on the cellular function or which inhibit or interfere with cell myosis, including alkylating agents, tumour necrosis factors, intercalators, microtubulin inhibitors and topoisomerase inhibitors. Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)mu-[diamine-platinum(II)]bis[diamine(chloro)platinum(II)] tetrachloride, diarizidinylspermine, arsenic trioxide, 1-(11-dodecylamino-10-hydroxyundecyl)-3,7-di-methylxanthine, zorubicin, idarubicin, daunorubicin, bisantrene, mitoxantrone, pirarubicin, pinafide, valrubicin, amrubicin, antineoplaston, 3'-de-amino-3'-morpholino-13-deoxo-10-hydroxycarminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Some examples of topoisomerase inhibitors are topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)dione, lurtotecan, 7-[2-(N-isopropylamino)ethyl]-(20S)-camptothecin, BNP1350, BNPI 1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido [4,3-b]carbazole-1-carboxamide, asulacrine, (5a,5aB,8aa, 9b)-9-[2-[N-[2-(dimethylamino)ethyl]-N-methylamino] ethyl]-5-[4-hydroxy-3,5-dimethoxy-phenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethyl-amino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASK-RAS, GEM231 and INX3001 and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1 ,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo-(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those already listed under "angiogenesis inhibitors", such as trastuzumab, and tumour suppressor genes, such as p53, which can be delivered via recombinant virus-mediated gene transfer (see U.S. Pat. No. 6,069,134, for example).

Above and below, all temperatures are indicated in ° C. In the following examples, "conventional work-up" means: water is added if necessary, the pH is adjusted, if necessary, to a value of between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) $M^+$FAB (fast atom bombardment) $(M+H)^+$ESI (electrospray ionisation) $(M+H)^+$(unless indicated otherwise)

EXAMPLE 1

The compounds according to the invention described in the examples were tested in the assays described below and were found to have kinase inhibitory activity. Other assays are known from the literature and could readily be performed by the person skilled in the art (see, for example, Dhanabal et al., Cancer Res. 59:189-197; Xin et al., J. Biol. Chem. 274:9116-9121; Sheu et al., Anticancer Res. 18:4435-4441; Ausprunk et al., Dev. Biol. 38:237-248; Gimbrone et al., J. Natl. Cancer Inst. 52:413-427; Nicosia et al., In Vitro 18:538-549).

VEGF Receptor Kinase Assay

VEGF receptor kinase activity is measured by incorporation of radiolabelled phosphate into 4:1 polyglutamic acid/tyrosine substrate (pEY). The phosphorylated pEY product is trapped onto a filter membrane and the incorporation of radiolabelled phosphate is quantified by scintillation counting.

VEGF Receptor Kinase

The intracellular tyrosine kinase domains of human KDR (Terman, B. I. et al. Oncogene (1991) Vol. 6, pp.1677-1683.) and Flt-1 (Shibuya, M. et al. Oncogene (1990) Vol. 5, pp. 519-524) were cloned as glutathione S-transferase (GST) gene fusion proteins. This was accomplished by cloning the cytoplasmic domain of the KDR kinase as an in frame fusion at the carboxyl terminus of the GST gene. Soluble recombinant GST-kinase domain fusion proteins were expressed in *Spodoptera frugiperda* (Sf21) insect cells (Invitrogen) using a baculovirus expression vector (pAcG2T, Pharmingen).

Lysis buffer: 50 mM Tris pH 7.4, 0.5 M NaCl, 5 mM DTT, 1 mM EDTA, 0.5% of Triton X-100, 10% of glycerol, 10 mg/ml each of leupeptin, pepstatin and aprotinin and 1 mM phenylmethylsulfonyl fluoride (all Sigma).

Wash buffer: 50 mM Tris pH 7.4, 0.5 M NaCl, 5 mM DTT, 1 mM EDTA, 0.05% of Triton X-100, 10% of glycerol, 10 mg/ml each of leupeptin, pepstatin and aprotinin and 1 mM phenylmethylsulfonyl fluoride.

Dialysis buffer: 50 mM Tris pH 7.4, 0.5 M NaCl, 5 mM DTT, 1 mM EDTA, 0.05% of Triton X-100, 50% of glycerol, 10 mg/ml each of leupeptin, pepstatin and aprotinin and 1 mM phenylmethylsulfonyl fluoride.

10× reaction buffer: 200 mM Tris, pH 7.4, 1.0 M NaCl, 50 mM $MnCl_2$, 10 mM DTT and 5 mg/ml of bovine serum albumin [BSA] (Sigma).

Enzyme dilution buffer: 50 mM Tris, pH 7.4, 0.1 M NaCl, 1 mM DTT, 10% of glycerol, 100 mg/ml of BSA.

10× substrate: 750 µg/ml of poly(glutamic acid/tyrosine; 4:1) (Sigma).

Stop solution: 30% of trichloroacetic acid, 0.2 M sodium pyrophosphate (both Fisher).

Wash solution: 15% of trichloroacetic acid, 0.2 M sodium pyrophosphate.

Filter plates: Millipore #MAFC NOB, GF/C glass fibre 96 well plate.

Method A—Protein Purification:
1. Sf21 cells are infected with the recombinant virus at a multiplicity of infection of 5 virus particles/cell and grown at 27° C. for 48 hours.
2. All steps are performed at 4° C. Infected cells are harvested by centrifugation at 1000× g and lysed at 4° C. for 30 minutes with ⅒ volume of lysis buffer followed by centrifugation at 100,000× g for 1 hour. The supernatant is then passed over a glutathione Sepharose column (Pharmacia) equilibrated with lysis buffer and washed with 5 volumes of the same buffer followed by 5 volumes of wash buffer. Recombinant GST-KDR protein is eluted with wash buffer/10 mM reduced glutathione (Sigma) and dialysed against dialysis buffer.

Method B—VEGF Receptor Kinase Assay:
1. Add 5 µl of inhibitor or control to the assay in 50% DMSO.
2. Add 35 µl, of reaction mixture containing 5 µl, of 10× reaction buffer, 5 µl of 25 mM ATP/10 µCi[$^{33}$P]ATP (Amersham) and 5 µl of 10× substrate.
3. Start reaction by addition of 10 µl of KDR (25 nM) in enzyme dilution buffer.
4. Mix and incubate at room temperature for 15 minutes.
5. Stop reaction by the addition of 50 µl of stop solution.
6. Incubate at 4° C. for 15 minutes.
7. Transfer a 90 µl aliquot to filter plate.
8. Aspirate and wash 3 times with wash solution.
9. Add 30 µl of scintillation cocktail, seal plate and count in a Wallac Microbeta scintillation counter.

Human Umbilical Vein Endothelial Cell Mitogenesis Assay:

Expression of VEGF receptors that mediate mitogenic responses to the growth factor is largely restricted to vascular endothelial cells. Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

HUVECs

HUVECs frozen as primary culture isolates are purchased from Clonetics Corp. Cells are maintained in endothelial growth medium (EGM; Clonetics) and are used for mitogenic assays at passages 3-7.

Culture plates: NUNCLON 96-well polystyrene tissue culture plates (NUNC #167008).

Assay medium: Dulbecco's modified Eagle medium containing 1 g/ml of glucose (low-glucose DMEM; Mediatech) plus 10% (v/v) of foetal bovine serum (Clonetics).

Test compounds: Working stock solutions of test compounds are diluted serially in 100% dimethyl sulfoxide (DMSO) to 400 times greater than their desired final concentrations. Final dilutions to 1× concentration are made in assay medium immediately prior to addition to cells.

10× growth factors: Solutions of human VEGF 165 (500 ng/ml; R&D Systems) and bFGF (10 ng/ml; R&D Systems) are prepared in assay medium.

10× [$^3$H]thymidine: [Methyl-$^3$H]thymidine (20 Ci/mmol; Dupont-NEN) is diluted to 80 µCi/ml in low-glucose DMEM medium.

Cell wash medium: Hank's balanced salt solution (Mediatech) containing 1 mg/ml bovine serum albumin (Boehringer-Mannheim).

Cell lysis solution: 1 N NaOH, 2% (w/v) $Na_2CO_3$.

Method 1

HUVEC monolayers maintained in EGM are harvested by trypsinisation and plated out at a density of 4000 cells per 100 µl of assay medium per well in 96-well plates. Cell growth is arrested for 24 hours at 37° C. in a humidified atmosphere containing 5% $CO_2$.

Method 2

Growth-arrest medium is replaced by 100 µl of assay medium containing either vehicle (0.25% [v/v] DMSO) or the desired final concentration of test compound. All determinations are performed in triplicate. Cells are then incubated at 37° C./5% $CO_2$ for 2 hours to allow test compounds to enter cells.

Method 3

After the 2-hour pre-treatment period, cells are stimulated by addition of 10 µl/well of either assay medium, 10× VEGF solution or 10× bFGF solution. Cells are then incubated at 37° C./5% $CO_2$.

Method 4

After 24 hours in the presence of growth factors, 10× [$^3$H]thymidine (10 µl/well) is added.

Method 5

Three days after addition of [$^3$H]thymidine, medium is removed by aspiration, and cells are washed twice with cell wash medium (400 µl/well followed by 200 µl/well). The washed, adherent cells are then solubilised by addition of cell lysis solution (100 µl/well) and warming to 37° C. for 30 minutes. Cell lysates are transferred to 7 ml glass scintillation vials containing 150 µl of water. Scintillation cocktail (5 ml/vial) is added, and cell-associated radioactivity is determined by liquid scintillation spectroscopy. According to these assays, the compounds of the formula I are inhibitors of VEGF and are thus suitable for the inhibition of angiogenesis, such as in the treatment of ocular diseases, for example diabetic retinopathy, and for the treatment of carcinomas, for example solid tumours. The present compounds inhibit VEGF-stimulated mitogenesis of human vascular endothelial cells in culture with IC50 values of 0.01-5.0 µM. These compounds also show selectivity over related tyrosine kinases (for example FGFR1 and the Src family; for relationship between Src kinases and VEGFR kinases, see Eliceiri et al., Molecular Cell, Vol. 4, pp.915-924, December 1999).

The TIE-2 tests can be carried out, for example, analogously to the methods indicated in WO 02/44156.

The assay determines the inhibiting activity of the substances to be tested in the phosphorylation of the substrate poly(Glu, Tyr) by Tie-2 kinase in the presence of radioactive $^{33}$P-ATP. The phosphorylated substrate binds to the surface of a "flashplate" microtitre plate during the incubation time. After removal of the reaction mixture, the microtitre plate is washed a number of times and the radioactivity on its surface is subsequently measured. An inhibiting effect of the substances to be measured results in lower radioactivity compared with an undisturbed enzymatic reaction.

EXAMPLE 2

Preparation of (5-chloro-7-nitrobenzoxazol-2-yl)-[4-(pyridin-4-ylsulfanyl)phenyl]amine The preparation is carried out analogously to the following scheme

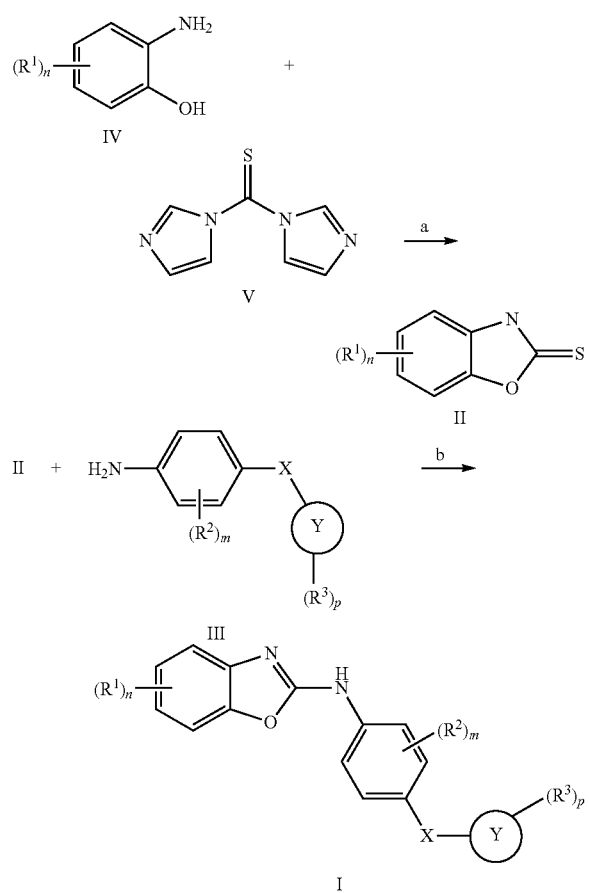

a 2 g of 2-amino-4-chloro-6-nitrophenol and 0.92 g of diimidazol-1-yl-methanethione are dissolved in 35 ml of dichloromethane and 15 ml of dimethylformamide and stirred overnight at room temperature. The solution is extracted with 1 N HCl. The organic phase is dried using MgSO$_4$, filtered and evaporated to dryness under reduced pressure, giving 1.56 g of 5-chloro-7-nitro-3H-benzoxazole-2-thione.

100 mg of 5-chloro-7-nitro-3H-benzoxazole-2-thione and 88 mg of 4-(pyridin-4-ylsulfanyl)phenylamine are dissolved in 3 ml of dimethylformamide and stirred overnight at 110° C. The mixture is evaporated to dryness under reduced pressure, and the residue is purified with the aid of preparative HPLC, giving 40 mg of (5-chloro-7-nitrobenzoxazol-2-yl)-[4-(pyridin-4-ylsulfanyl)phenyl]-amine, an amorphous solid substance; retention time: 3.68 minutes, EI-MS (M+H)$^+$ 399.

Method for the determination of the retention time:
Column: Chromolith SpeedROD, 50×4.6 mm$^2$ from Merck
Eluent: A: H$_2$O, 0.1% of TFA
B: acetonitrile, 0.08% of TFA
Wavelength: 220 nm
Gradient: 5.0 min, t=0 min, A:B=95:5, t=4.4 min: A:B=25:75, t=4.5 min to t=5.0 min: A:B=0:100
Flow rate: 3.00 ml/min The following compounds are obtained analogously

| Compound | Mol. weight EI-MS (M + H)$^+$ | Retention time (min) |
|---|---|---|
| Benzoxazol-2-yl-[4-(pyridin-4-yloxy)phenyl]amine | 3.03E+02 | 2.93 |
| Benzoxazol-2-yl-[4-(pyridin-4-ylsulfanyl)phenyl]-amine | 3.19E+02 | 3.15 |

-continued

| Compound | Mol. weight EI-MS (M + H)+ | Retention time (min) |
|---|---|---|
| 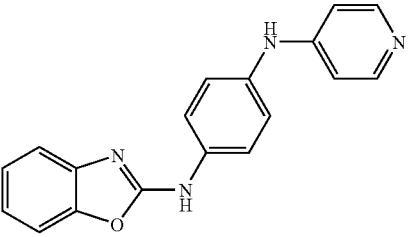<br>N-Benzoxazol-2-yl-N'-pyridin-4-ylbenzene-1,4-diamine | 3.02E+02 | 2.75 |
| 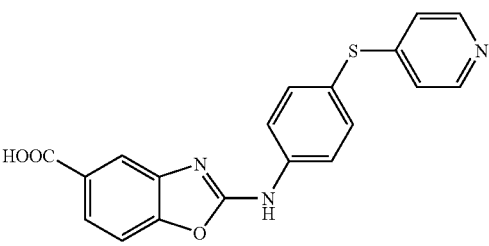<br>2-[4-(Pyridin-4-ylsulfanyl)phenylamino]benzoxazole-5-carboxylic acid | 3.63E+02 | 2.72 |
| 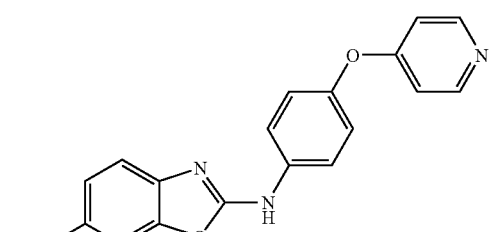<br>2-[4-(Pyridin-4-yloxy)phenylamino]benzoxazole-6-carboxylic acid | 3.47E+02 | 2.4 |
| 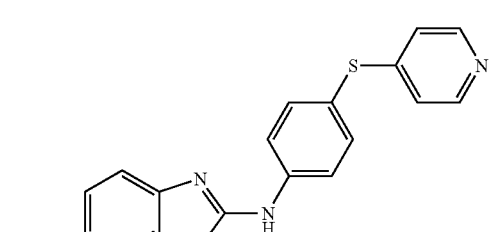<br>2-[4-(Pyridin-4-ylsulfanyl)phenylamino]benzoxazole-6-carboxylic acid | 3.63E+02 | 2.69 |
| 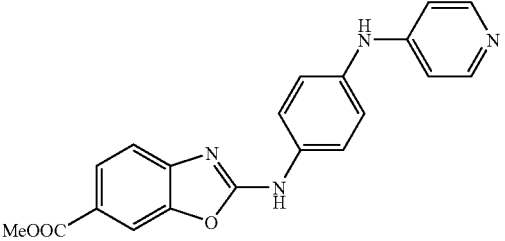<br>Methyl 2-[4-(pyridin-4-ylamino)phenylamino]-benzoxazole-6-carboxylate | 3.60E+02 | 2.83 |

-continued
| Compound | Mol. weight EI-MS (M + H)⁺ | Retention time (min) |
|---|---|---|
| 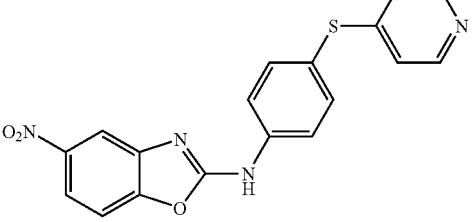 (5-Nitrobenzoxazol-2-yl)-[4-(pyridin-4-ylsulfanyl)-phenyl]amine | 3.64E+02 | 3.28 |
| 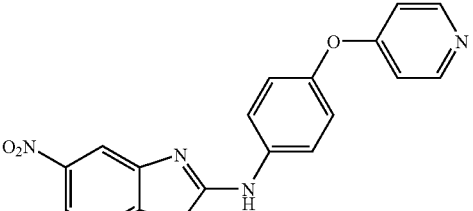 (5-Nitrobenzoxazol-2-yl)-[4-(pyridin-4-yloxy)-phenyl]amine | 3.48E+02 | 3.12 |
| 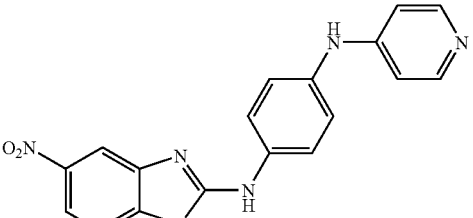 N-(5-Nitrobenzoxazol-2-yl)-N'-pyridin-4-yl-benzene-1,4-diamine | 3.47E+02 | 3.09 |
| 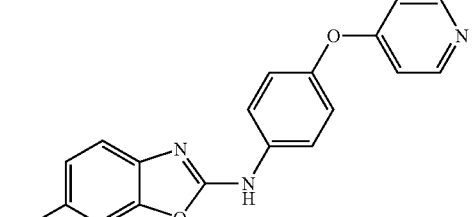 (6-Nitrobenzoxazol-2-yl)-[4-(pyridin-4-yloxy)-phenyl]amine | 3.48E+02 | 3.07 |
| 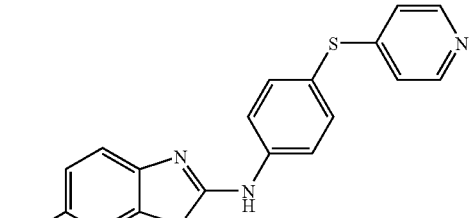 (6-Nitrobenzoxazol-2-yl)-[4-(pyridin-4-ylsulfanyl)-phenyl]amine | 3.64E+02 | 3.2 |

-continued
| Compound | Mol. weight EI-MS $(M+H)^+$ | Retention time (min) |
|---|---|---|
| 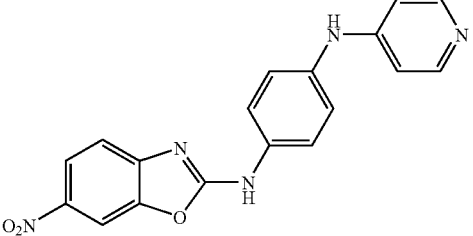<br>N-(6-Nitrobenzoxazol-2-yl)-N'-pyridin-4-yl-benzene-1,4-diamine | 3.47E+02 | 2.93 |
| 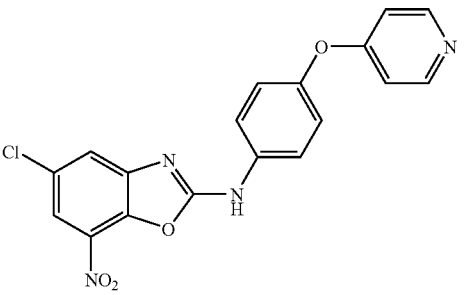<br>(5-Chloro-7-nitrobenzoxazol-2-yl)-[4-(pyridin-4-yl-oxy)phenyl]amine | 3.83E+02 | 3.44 |
| 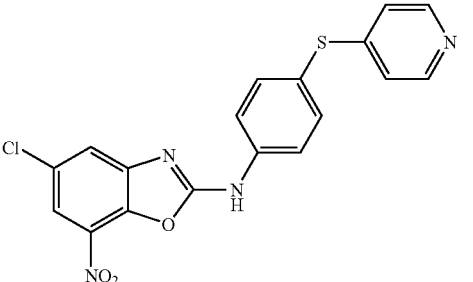<br>(5-Chloro-7-nitrobenzoxazol-2-yl)-[4-(pyridin-4-yl-sulfanyl)phenyl]amine | 3.99E+02 | 3.68 |
| 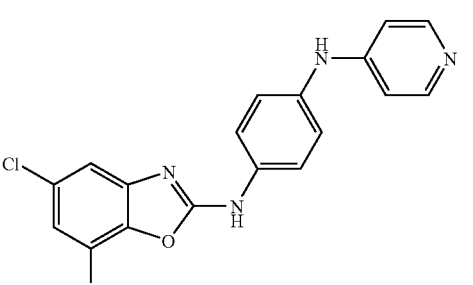<br>N-(5-Chloro-7-nitrobenzoxazol-2-yl)-N'-pyridin-4-ylbenzene-1,4-diamine | 3.82E+02 | 3.49 |

-continued

| Compound | Mol. weight EI-MS $(M+H)^+$ | Retention time (min) |
|---|---|---|
| 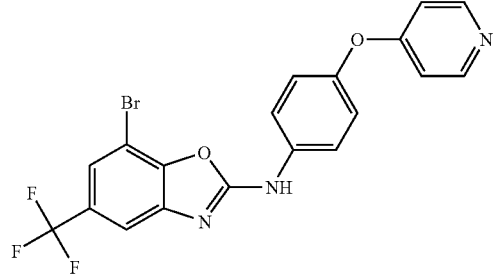<br>(7-Bromo-5-trifluoromethylbenzoxazol-2-yl)-[4-(pyridin-4-yloxy)phenyl]amine | 4.50E+02 | 3.84 |
| 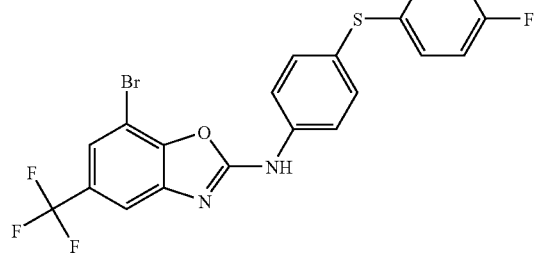<br>(7-Bromo-5-trifluoromethylbenzoxazol-2-yl)-[4-(pyridin-4-ylsulfanyl)phenyl]amine | 4.66E+02 | 4.05 |
| 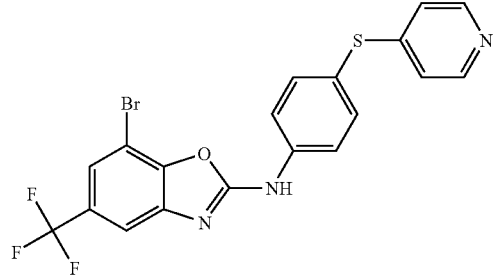<br>(7-Bromo-5-trifluoromethylbenzoxazol-2-yl)-[4-(4-fluorophenylsulfanyl)phenyl]amine | 483E+02 | 5.65 |
| 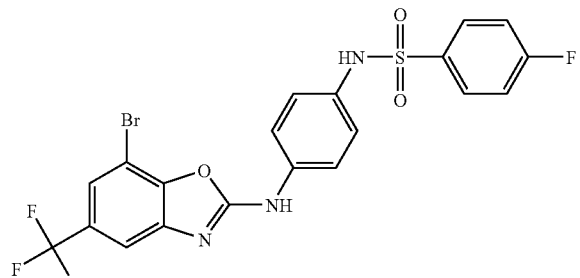<br>N-[4-(Bromotrifluoromethylbenzoxazol-2-yl-amino)phenyl]-4-fluorobenzenesulfonamide | 5.30E+02 | 5.01 |

| Compound | Mol. weight EI-MS (M + H)+ | Retention time (min) |
|---|---|---|
| 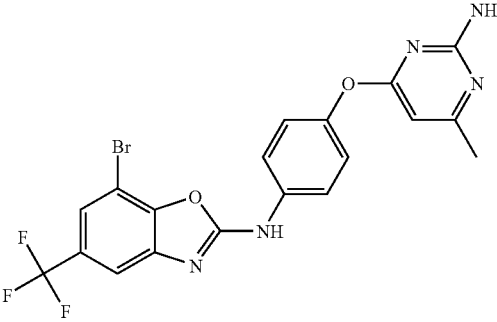<br>[4-(2-Amino-6-methylpyrimidin-4-yloxy)phenyl]-(7-bromo-5-trifluoromethylbenzoxazol-2-yl)-amine | 4.80E+02 | 4.08 |
| 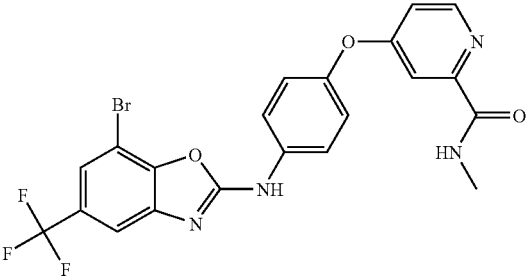<br>N-Methyl-4-[4-(bromotrifluoromethylbenzoxazol-2-ylamino)phenoxy]pyridine-2-carboxamide | 5.07E+02 | 4.72 |
| 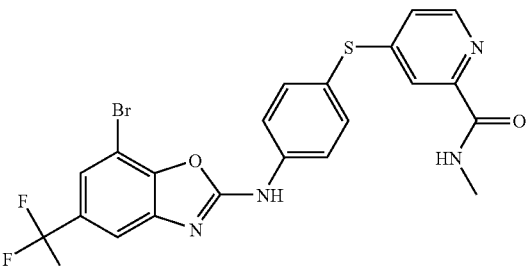<br>N-Methyl-4-[4-(bromotrifluoromethylbenzoxazol-2-ylamino)phenylsulfanyl]pyridine-2-carboxamide | 5.23E+02 | 5.15 |
| 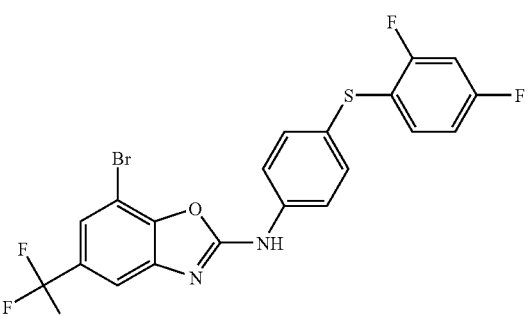<br>(7-Bromo-5-trifluoromethylbenzoxazol-2-yl)-[4-(2,4-difluorophenylsulfanyl)phenyl]amine | 5.01E+02 | 5.6 |

EXAMPLE 3

Pharmacological Test Results

| Compound | Inhibition of TIE-2 IC$_{50}$ (nmol) | Inhibition of RAF IC$_{50}$ (nmol) |
|---|---|---|
| (5-Chloro-7-nitrobenzoxazol-2-yl)-[4-(pyridin-4-ylsulfanyl)phenyl]amine | 310 | >1000 |

The following examples relate to pharmaceutical compositions:

EXAMPLE 4

Injection Vials

A solution of 100 g of an active ingredient according to the invention and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE 5

Suppositories

A mixture of 20 g of an active ingredient according to the invention with 100 g of soya lecithin and 1400 g of cocoa butter is melted, poured into moulds and allowed to cool. Each suppository contains 20 mg of active ingredient.

EXAMPLE 6

Solution

A solution is prepared from 1 g of an active ingredient according to the invention, 9.38 g of NaH$_2$PO$_4$. 2 H$_2$O, 28.48 g of Na$_2$HPO$_4$. 12 H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE 7

Ointment 500 mg of an active ingredient according to the invention are mixed with 99.5 g of Vaseline under aseptic conditions.

EXAMPLE 8

Tablets

A mixture of 1 kg of active ingredient, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE 9

Coated Tablets

Tablets are pressed analogously to Example E and subsequently coated in a conventional manner with a coating of sucrose, potato starch, talc, tragacanth and dye.

EXAMPLE 10

Capsules 2 kg of active ingredient are introduced into hard gelatine capsules in a conventional manner in such a way that each capsule contains 20 mg of the active ingredient.

EXAMPLE 11

Ampoules

A solution of 1 kg of an active ingredient according to the invention in 60 l of bidistilled water is sterile filtered, transferred into ampoules, lyophilised under sterile conditions and sealed under sterile conditions. Each ampoule contains 10 mg of active ingredient.

The invention claimed is:
1. A compound of formula I

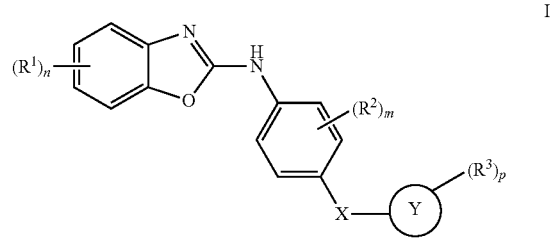

in which
R$^1$ is Hal, NO$_2$, CF$_3$, COOH, COOR or H,
R$^2$ is R, Hal, CN, NO$_2$, NHR, NRR, NHCOR, NHSO$_2$R, OR, CO—R, CO—NHR, CF$_3$, OCF$_3$, SCF$_3$, SO$_3$R, SO$_2$R, SO$_2$NR, SR, COOH or COOR,
R$^3$ is Hal or CO—NHR,
R is H or unsubstituted or mono-, di-, tri- or tetra-R$^4$-substituted A, Ar, Het, (CH$_2$)$_q$Het or (CH$_2$)$_q$Ar,
A is unbranched, branched or cyclic alkyl having 1-14 C atoms, in which one or two CH$_2$ groups are each optionally replaced by O, S, or —CH=CH— and/or 1-7 H atoms are each optionally replaced by F or Cl,
Ar is phenyl, naphthyl or biphenyl, each of which is unsubstituted or mono-, di- or trisubstituted by A, Hal, OH, OA, CN, NO$_2$, NH$_2$, NHA, NA$_2$, NHCOA, SCF$_3$, SO$_2$A, COOH, COOA, CONH$_2$, CONHA, CONA$_2$, NHSO$_2$A, SO$_2$NH$_2$, SO$_2$NHA, SO$_2$NA$_2$, CHO or COA,
Het is a mono- or bicyclic saturated, unsaturated or aromatic heterocycle having 1 to 4 N, O and/or S atoms, which may be unsubstituted or mono-, di- or trisubstituted by carbonyl oxygen, Hal, A,—(CH$_2$)$_b$—Ar, —(CH$_2$)$_b$-cycloalkyl, OH, OA, NH$_2$, NHA, NA$_2$, NO$_2$, CN, COOH, COOA, CONH$_2$, CONHA, CONA$_2$, NHCOA, NHCONH$_2$, NHSO$_2$A, CHO, COA, SO$_2$NH$_2$ and/or S(O)$_g$A, Hal is F, Cl, Br or I, R$^4$ is Hal, OH, CN, NO$_2$, CF$_3$, OCF$_3$, SCF$_3$, SO$_2$A or OA, X is O, S, or NH, Y is phenyl or a monocyclic aromatic heterocycle having 1 to 4 N, O and/or S atoms, b is 0, 1, 2, 3 or 4, g is 0, 1 or 2, n, m, p, q are each, independently of one another, 1, 2, 3, or 4, or a pharmaceutically acceptable salt, or stereoisomer thereof, including mixtures of stereoisomers in all ratios.

2. A compound according to claim 1, in which R$^2$ is H.

3. A compound according to claim 1, in which Y is phenyl, furyl, thienyl, pyrrolyl, imidazolyl, pyridyl or pyrimidinyl.

4. A compound according to claim 1, in which
R$^2$ is H,
Y is phenyl, furyl, thienyl, pyrrolyl, imidazolyl, pyridyl or pyrimidinyl,
X is O, S, or NH,
n, p, are each, independently of one another, 1, 2, 3 or 4,
m is 1.

5. A compound according to claim 1, wherein A is methyl, ethyl, propyl, isopropyl, butyl, isobutyl, sec-butyl, tert-butyl, pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-l-methylpropyl, 1-ethyl-2-methylpropyl, 1,1,2- or 1,2,2-trimethylpropyl, linear or branched heptyl, octyl, nonyl, decyl, trifluoromethyl, pentafluoroethyl, 1,1,1-trifluoroethyl, cyclopropyl, cyclobutyl, cyclopentyl, cyclohexyl, or cycloheptyl.

6. A compound according to claim 5, wherein A is methyl, ethyl, propyl, isopropyl, butyl, isobutyl, sec-butyl, or tert-butyl.

7. A compound according to claim 5, wherein A is methyl, ethyl, propyl, isopropyl, butyl, isobutyl, sec-butyl, tert-butyl, pentyl, hexyl, trifluoromethyl, pentafluoroethyl, or 1,1,1-trifluoroethyl.

8. A compound according to claim 1, wherein A is alkyl having 1, 2, 3, 4, 5 or 6 C atoms, in which one or two CH$_2$ groups are each optionally replaced by O, S, or by —CH═CH—, and 1-7 H are each optionally replaced by F or Cl.

9. A compound according to claim 1, wherein Ar is phenyl, naphthyl or biphenyl, which in each case is mono-, di- or trisubstituted by substituents selected from A, fluorine, chlorine, bromine, iodine, hydroxyl, methoxy, ethoxy, propoxy, butoxy, pentyloxy, hexyloxy, nitro, cyano, formyl, acetyl, propionyl, tri-fluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, and aminocarbonyl.

10. A compound according to claim 1, wherein Het is 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-iso-thiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7- benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl, or 2,1,3-benzoxadiazol-5-yl, which in each case is unsubstituted or mono-, di- or trisubstituted by substituents selected from carbonyl oxygen, F, Cl, Br, methyl, ethyl, propyl, phenyl, benzyl, -CH$_2$-cyclohexyl, hydroxyl, methoxy, ethoxy, amino, methylamino, dimethylamino, nitro, cyano, carboxyl, methoxycarbonyl, aminocarbonyl, methylaminocarbonyl, dimethylaminocarbonyl, acetamino, ureido, methylsulfonylamino, formyl, acetyl, aminosulfonyl, and methylsulfonyl, or Het is 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-,- 2-,-3-, -4-, -5-, -6-, -7- or -8-isoquinolyl, 2-, 3-, 5-, 6-, 7- or 8- 3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl, 3,4-dihydro-2H-1,5-benzodioxepin-6- or -7-yl, 2,3-dihydrobenzofuranyl, 2,3-dihydro-2-oxofuranyl, 2-oxopiperidin-l-yl, 2-oxopyrrolidin-l-yl, 2-oxo-1H-pyridin-l-yl, 3-oxomorpholin-4-yl, 4-oxo-1H-pyridin-l-yl, 2,6-dioxopiperidinl-yl, 2-oxopiperazin-l-yl, 2,6-dioxopiperazin-l-yl, 2,5-dioxopyrrolidin-l-yl, 2-oxo-1,3-oxazolidin-3-yl, 3-oxo-2H-pyridazin-2-yl, 2-caprolactam-l-yl, 2-hydroxy-6-oxopiperazin-l-yl, 2-methoxy-6-oxopiperazin-l-yl, or 2-azabicyclo[2.2.2]octan-3-on-2-yl.

11. A compound according to claim 10, wherein
A is methyl, ethyl, propyl, isopropyl, butyl, isobutyl, sec-butyl, tert-butyl, pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-l-methylpropyl, 1-ethyl-2-methylpropyl, 1,1,2- or 1,2,2-trimethylpropyl, linear or branched heptyl, octyl, nonyl, decyl, trifluoromethyl, pentafluoroethyl, 1,1,1-trifluoroethyl, cyclopropyl, cyclobutyl, cyclopentyl, cyclohexyl, or cycloheptyl; and Ar is phenyl, naphthyl or biphenyl, which in each case is mono-, di- or trisubstituted by substituents selected from A, fluorine, chlorine, bromine, iodine, hydroxyl, methoxy, ethoxy, propoxy, butoxy, pentyloxy, hexyloxy, nitro, cyano, formyl, acetyl, propionyl, tri-fluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, and aminocarbonyl.

12. A compound according to claim 1, wherein Y is phenyl, pyridyl or pyrimidinyl.

13. A compound according to claim 1, in which
$R^1$ is Hal, $NO_2$, $CF_3$, COOH, COOR or H,
$R^2$ is H,
Y is phenyl, furyl, thienyl, pyrrolyl, imidazolyl, pyridyl or pyrimidinyl, and
X is O, S, or NH.

14. A compound selected from:
benzoxazol-2-yl-[4-(pyridin-4-yloxy)phenyll]amine,
benzoxazol-2-yl-[4-(pyridin-4-ylsulfanyl)phenyll]amine,
N-benzoxazol-2-yl-N'-pyridin-4-ylbenzene-1,4-diamine,
2-[4-(pyridin-4-ylsulfanyl)phenylamino]benzoxazole-5-carboxylic acid,
2-[4-(pyridin-4-yloxy)phenylamino]benzoxazole-6-carboxylic acid,
2-[4-(pyridin-4-ylsulfanyl)phenylamino]benzoxazole-6-carboxylic acid,
methyl 2-[4-(pyridin-4-ylamino)phenylamino]benzoxazole-6-carboxylate,
(5-nitrobenzoxazol-2-yl)-[4-(pyridin-4-ylsulfanyl)phenyl]amine,
(5-nitrobenzoxazol-2-yl)-[4-(pyridin-4-yloxy)phenyl]amine,
N-(5-nitrobenzoxazol-2-yl)-N'-pyridin-4-ylbenzene-1,4-diamine,
(6-nitrobenzoxazol-2-yl)-[4-(pyridin-4-yloxy)phenyl]amine,
(6-nitrobenzoxazol-2-yl)-[4-(pyridin-4-ylsulfanyl)phenyl]amine,
N-(6-nitrobenzoxazol-2-yl)-N'-pyridin-4-ylbenzene-1,4-diamine,
(5-chloro-7-nitrobenzoxazol-2-yl)-[4-(pyridin-4-yloxy)phenyl]amine,
(5-chloro-7-nitrobenzoxazol-2-yl)-[4-(pyridin-4-ylsulfanyl)phenyl]-amine,
N-(5-chloro-7-nitrobenzoxazol-2-yl)-N'-pyridin-4-ylbenzene-1,4-diamine,
(7-bromo-5-trifluoromethylbenzoxazol-2-yl)-[4-(pyridin-4-yloxy)phenyl]-amine,
(7-bromo-5-trifluoromethylbenzoxazol-2-yl)-[4-(pyridin-4-ylsulfanyl)phenyl]-amine,
(7-bromo-5-trifluoromethylbenzoxazol-2-yl)-[4-(4-fluorophenylsulfanyl)-phenyl]amine,
N-[4-(bromotrifluoromethylbenzoxazol-2-ylamino)phenyl]-4-fluoro-benzenesulfonamide, [4-(2-amino-6-methylpyrimidin-4-yloxy)phenyl]-(7-bromo-5-trifluoromethylbenzoxazol-2-yl)amine,
N-methyl-4-[4-(bromotrifluoromethylbenzoxazol-2-ylamino)phenoxyl]-pyridine-2-carboxamide,
N-methyl-4-[4-(bromotrifluoromethylbenzoxazol-2-ylamino)phenylsulfanyl]-pyridine-2-carboxamide, and
(7-bromo-5-trifluoromethylbenzoxazol-2-yl)-[4-(2,4-difluorophenylsulfanyl)-phenyl]amine,
and pharmaceutically acceptable salts, and stereoisomers thereof, including mixtures of stereoisomers in all ratios.

15. A pharmaceutical composition comprising at least one compound according to claim 1 and one or more excipients and/or adjuvants.

16. A pharmaceutical composition comprising at least one compound according to claim 1, and at least one active ingredient in addition to said one compound according to claim 1.

17. A kit consisting of separate packs of a) an effective amount of a compound according to claim 1, and b) an effective amount of an active ingredient in addition to said compound according to claim 1.

18. A process for preparation of a compound according to claim 1, said process comprising:
reacting a compound of formula II

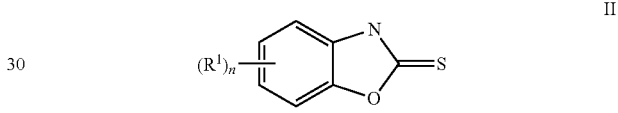

II with a compound of formula III

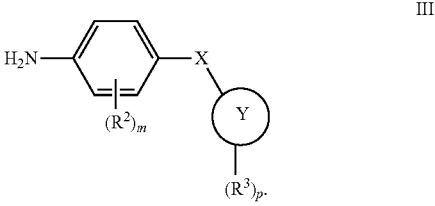

III

* * * * *

UNITED STATES PATENT AND TRADEMARK OFFICE
CERTIFICATE OF CORRECTION

PATENT NO. : 8,242,128 B2
APPLICATION NO. : 10/573176
DATED : August 14, 2012
INVENTOR(S) : Wolfgang Stahle et al.

It is certified that error appears in the above-identified patent and that said Letters Patent is hereby corrected as shown below:

Column 45, line 14 (Claim 14), reads: "benzoxazol-2-yl-[4-(pyridin-4-yloxy)phenyll]amine,"
It should read: -- benzoxazol-2-yl-[4-(pyridin-4-yloxy)phenyl]amine, --

Column 45, line 15 (Claim 14), reads: "benzoxazol-2-yl-[4-(pyridin-4-ylsulfanyl)phenyll]amine,"
It should read: -- benzoxazol-2-yl-[4-(pyridin-4-ylsulfanyl)phenyl]amine, --

Column 46, lines 2-4 (Claim 14), read:
"nyl]-4-fluoro-benzenesulfonamide, [4-(2-amino-6-me-
thylpyrimidin-4-yloxy)phenyl]-(7-bromo-5-trifluoro-
methylbenzoxazol-2-yl)-amine,"

It should read:
-- nyl]-4-fluoro-benzenesulfonamide,
[4-(2-amino-6-me-thylpyrimidin-4-yloxy)phenyl]-(7-bromo-5-trifluoro-methylbenzoxazol-2-yl)-
amine, --

Signed and Sealed this
Twenty-seventh Day of November, 2012

David J. Kappos
*Director of the United States Patent and Trademark Office*